(12) United States Patent
Bouvier et al.

(10) Patent No.: US 8,883,486 B2
(45) Date of Patent: *Nov. 11, 2014

(54) ARRESTIN BIOSENSOR

(75) Inventors: Michel Bouvier, Montreal (CA); Pascale G. Charest, Tucson, AZ (US); Christian LeGouill, Montreal (CA); Alexandre Beautrait, Montreal (CA); Stephane Alain Laporte, Outremont (CA); Brandon Zimmerman, Brookline, MA (US)

(73) Assignee: Universite de Montreal, Montreal (CA)

( * ) Notice: Subject to any disclaimer, the term of this patent is extended or adjusted under 35 U.S.C. 154(b) by 507 days.

This patent is subject to a terminal disclaimer.

(21) Appl. No.: 13/092,667

(22) Filed: Apr. 22, 2011

(65) Prior Publication Data
US 2011/0275134 A1 Nov. 10, 2011

Related U.S. Application Data

(63) Continuation-in-part of application No. 11/579,482, filed as application No. PCT/CA2005/000695 on May 4, 2005, now Pat. No. 7,932,080.

(60) Provisional application No. 60/567,454, filed on May 4, 2004.

(51) Int. Cl.
| C12M 1/34 | (2006.01) |
| G01N 33/533 | (2006.01) |
| G01N 33/542 | (2006.01) |
| G01N 33/58 | (2006.01) |

(52) U.S. Cl.
CPC ............ *G01N 33/542* (2013.01); *G01N 33/533* (2013.01); *G01N 2333/4704* (2013.01); *G01N 2333/726* (2013.01); *G01N 33/582* (2013.01)
USPC .................................................... 435/287.1

(58) Field of Classification Search
CPC ....................................................... C12Q 1/66
USPC .................................................... 435/287.1
See application file for complete search history.

(56) References Cited

U.S. PATENT DOCUMENTS

| 5,654,419 | A | 8/1997 | Mathies et al. |
| 5,688,648 | A | 11/1997 | Mathies et al. |
| 5,853,992 | A | 12/1998 | Glazer et al. |
| 5,863,727 | A | 1/1999 | Lee et al. |
| 5,945,526 | A | 8/1999 | Lee et al. |
| 6,008,373 | A | 12/1999 | Waggoner et al. |
| 6,150,107 | A | 11/2000 | Glazer et al. |
| 6,177,249 | B1 | 1/2001 | Kwok et al. |
| 6,335,440 | B1 | 1/2002 | Lee et al. |
| 6,348,596 | B1 | 2/2002 | Lee et al. |
| 6,479,303 | B1 | 11/2002 | Waggoner et al. |
| 6,545,164 | B1 | 4/2003 | Waggoner et al. |
| 6,696,255 | B2 | 2/2004 | Dattagupta |
| 6,699,687 | B1 | 3/2004 | Tsien et al. |
| 6,849,745 | B2 | 2/2005 | Lee et al. |
| 6,908,769 | B2 | 6/2005 | Belik et al. |
| 7,842,469 | B2 | 11/2010 | Gambhir et al. |
| 2002/0168641 | A1 | 11/2002 | Mortensen et al. |
| 2003/0143594 | A1 | 7/2003 | Mathies et al. |
| 2004/0076979 | A1 | 4/2004 | Belik et al. |
| 2009/0123953 | A1 | 5/2009 | Bouvier et al. |

FOREIGN PATENT DOCUMENTS

CA 2335305 A1 12/1999

OTHER PUBLICATIONS

Vishnivetskiy et al. "Transition of arrestin into the active receptor-binding state requires an extended interdomain hinge", JBC, 2002, 277(46):43961-43967.*
Angers et al., Detection of β2-Adrenergic Receptor Dimerization in Living Cells Using Bioluminescence Resonanace Energy Transfer (BRET), PNAS, 2000, 97:3684-3689.
Azzi et al, β-Arrestin-Mediated Activation of MAPK by Inverse Agonists Reveals Distinct Active Conformations for G Protein-Coupled Receptors, PNAS, 2003, 100:11406-11411.
Barak et al., A βArrestin / Green Fluorescent Protein Biosensor for Detecting G Protein-Coupled Receptor Activation, Journal of Biological Chemistry, 1997, 272(44):27497-27500.
Bertrand et al., The BRET2/Arrestin Assay in Stable Recombinant Cells: A Platform to Screen for Compounds that Interact with G Protein-Coupled Receptors (GPCRs), Journal of Receptors and Signal Transduction, 2002, 22:533-541.
Charest et al., Palmitoylation of the V2 Vasopressin Receptor Carboxyl Tail Enhances β-Arrestin Recruitment Leading to Efficient Receptor Endocytosis and ERK1/2 Activation, Journal of Biological Chemistry, 2003, 278 (42):41541-41551.
Charest et al., Monitoring Agonist-Promoted Conformational Changes of β-Arrestin in Living Cells by intramolecular BRET, EMBO Reports, 2005, 6(4):334-340
Dalle et al., Insulin and Insulin-Like Growth Factor I Receptors Utilize Different G Protein Signaling Components, Journal of Biological Chemistry, 2001, 276(19)15688-15695.
Gurevich et al., Visual Arrestin Interaction with Rhodopsin, Sequential Multisite Binding Ensures Strict Selectivity Toward Light-Activated Phosphorylated Rhodopsin, Journal of Biological Chemistry, 1993, 268:11628-11638.
Han et al., Crystal Structure of β-Arrestin at 1.9 A: Possible Mechanism of Receptor Binding and Membrane Translocation, Structure, 2001 9:869-880.
Hebert et al., A Peptide Derived from a β2-Adrenergic Receptor Transmembrane Domain Inhibits Both Receptor Dimerization and Activation, Journal of Biological Chemistry, 1996, 271:16384-16392
Hirsch et al., The 2.8 A° Crystal Structure of Visual Arrestin: A Model for Arrestin's Regulation. Cell, 1999, 97:257-269.
Kovoor et al., Targeted Construction of Phosphorylation-Independent β-Arrestin Mutants with Constitutive Activity in Cells, Journal of Biological Chemistry, 1999, 274:6831-6834.
Kroeger et al., Constitutive and Agonist-Dependent Homo-Oligomerization of the Thyrotropin-Releasing Hormone Receptor, Journal of Biological Chemistry, 2001, 276(16):12736-12743.

(Continued)

*Primary Examiner* — Bin Shen
(74) *Attorney, Agent, or Firm* — Quarles & Brady LLP

(57) ABSTRACT

The present invention relates to a novel biosensor. A resonance energy transfer (RET) biosensor comprising a beta(β)-arrestin tagged with a first and a second chromophore, wherein said first chromophore is a fluorophore and said second chromophore is a fluorophore or a bioluminophore is described.

21 Claims, 15 Drawing Sheets

(56) References Cited

OTHER PUBLICATIONS

Leduc et al., Functional Selectivity of Natural and Synthetic Prostaglandin EP4 Receptor Ligands, Journal of Pharmacology and Experimental Therapeutics, 2009, 331(1):297-307.

Lefkowitz et al., β-Arrestins: Traffic Cops of Cell Signaling, Current Opinion in Cell Biology, 2004, 6:162-168.

Lefkowitz et al., Transduction of Receptor Signals by β-Arrestins, Science, 2005, 308:512-517.

Loening et al., Consensus Guided Mutagenesis Enhanced of Renilla Luciferase Yields Enhanced Stability and Light Output, Protein Engineering, Design & Selection, 2006, 19(9):391-400.

Lin et al., Feedback Regulation of β-Arrestin1 Function by Extracellular Signal-Regulated Kinases, Journal of Biological Chemistry, 1999, 274:15971-15974.

Luttrell et al., The Role of β-Arrestins in the Termination and Transduction of G-Protein-Coupled Receptor Signals, Journal of Cell Science, 2002, 115:455-465.

Marrache et al., Proinflammatory Gene induction by Platelet-Activating Factor Mediated Via Its Cognate Nuclear Receptor, Journal of Immunology, 2002, 169:6474-6461.

Mercier et al., Quantitative Assessment of β1- and β2-Adrenergic Receptor Homo- and Heterodimerization by Bioluminescence Resonance Energy Transfer, Journal of Biological Chemistry, 2002, 277:44925-44931.

Milligan, Applications of Bioluminescence- and Fluorescence Resonance Energy Transfer Drug Discovery at G Protein-Coupled Receptors, European Journal of Pharmaceutical Sciences, 2004, 21:397-405.

Nagai et al., Expanded Dynamic Range of Fluorescent Indicators for Ca2+ by Circularly Permuted Yellow Fluorescent Proteins, PNAS, 2004, 101(10554-10559.

Oakley et al., Differential Affinities of Visual Arrestin, β-Arrestin1, and β-Arrestin2 for G Protein-Coupled Receptors Delineate Two Major Classes of Receptors, Journal of Biological Chemistry, 2000, 275:17201-17210.

Oakley et al., Molecular Determinants Underlying the Formation Stable Intracellular G Protein-Coupled Receptor- β-Arrestin Complexes after Receptor Endocytosis, Journal of Biological Chemistry, 2001, 276:19452-19460.

Perroy et al., Phosphorylation-Independent Desensitization of GABA(B) Receptor by GRK4, EMBO Journal, 2003, 22:3816-3824.

Scott et al., Differential Nucleocytoplasmic Shuttling of β-Arrestins, Journal of Biological Chemisty, 2002, 277 (40):37693-37701.

Terrillon et al., Oxytocin and Vasopressin V1a and V2 Receptors Form Constitutive Homo- and Heterodimers During Biosynthesis, Molecular Endocrinology, 2003, 17:677-691.

Vishnivetskiy at al., Transition of Arrestin into the Active Receptor-Binding State Requires an Extended Interdomain Hinge, Journal of Biological Chemistry, 2002, 277:43961-43967.

Xiao et al., Activation-Dependent Conformational Changes in β-Arrestin 2, Journal of Biological Chemistry, 2004, 279:55744-55753.

Xu et al., A Bioluminescence Resonance Energy Transfer (BRET) System: Application to Interacting Circadian Clock Proteins, Proc. Natl. Acad, Sci. USA, 1999, 96:151-156.

Zhang of et al., Creating New Fluorescent Probes for Cell Biology, Nature Reviews Molecular Cell Biology, 2002, 3:906-918.

PCT International Search Report, PCT/CA2005/000695, Aug. 25, 2005.

* cited by examiner

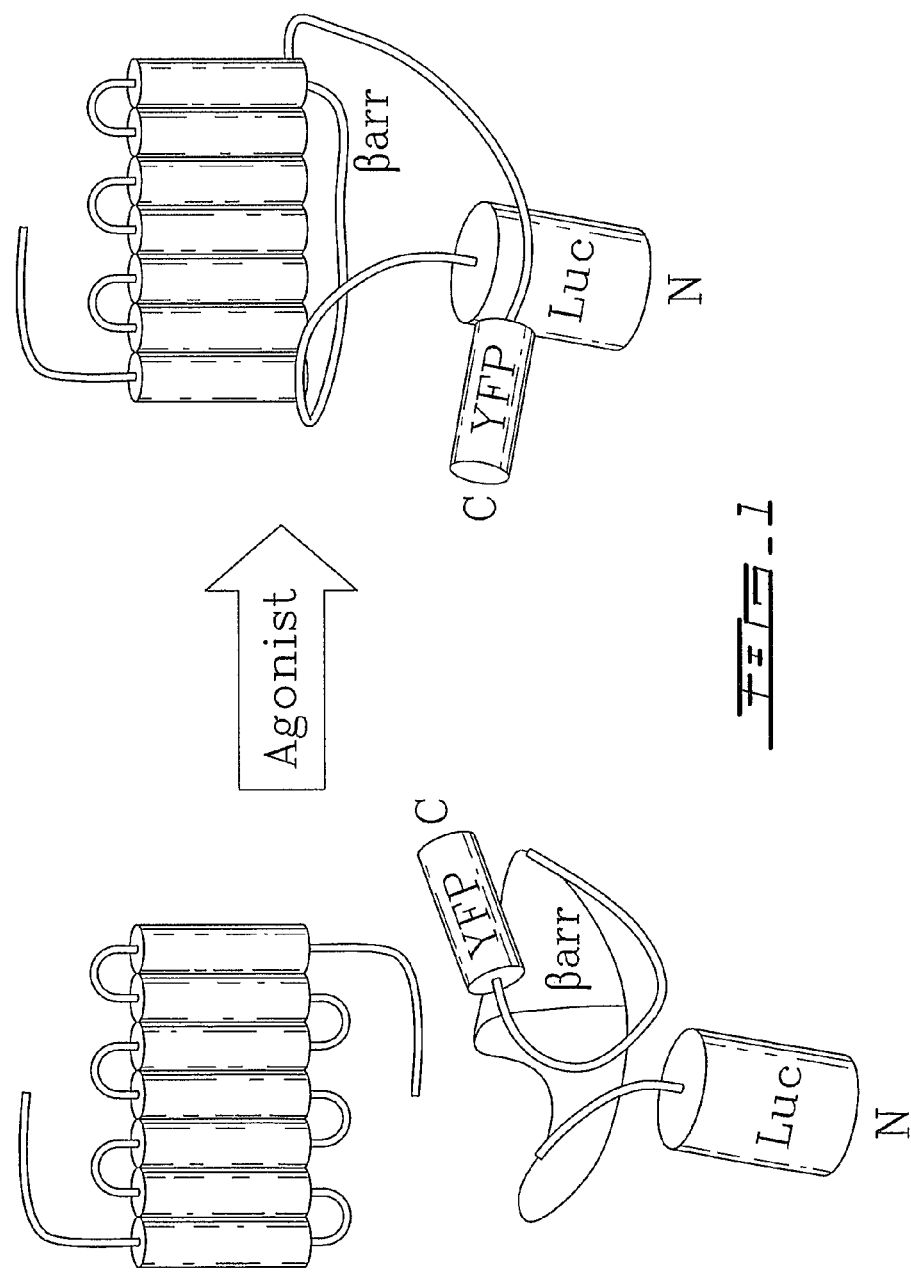

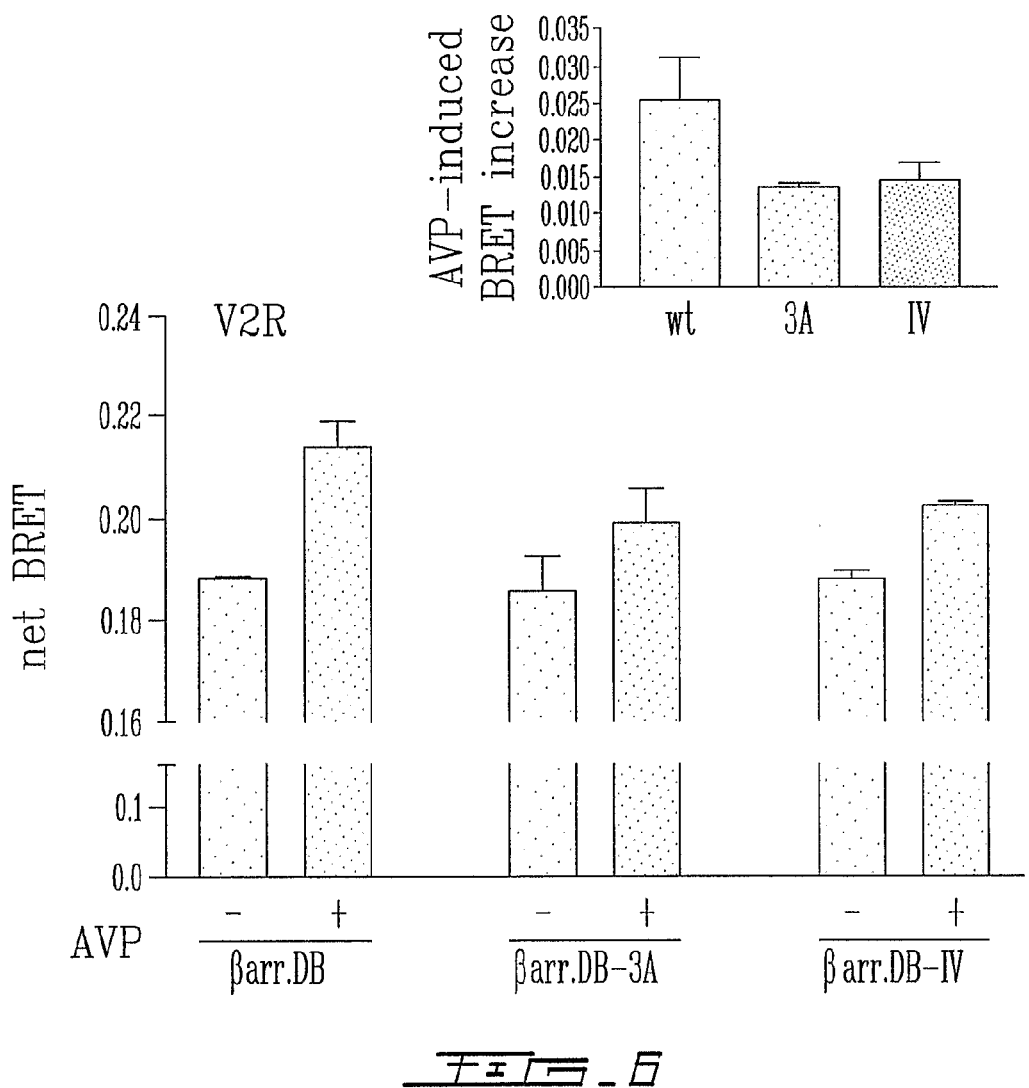
FIG_6

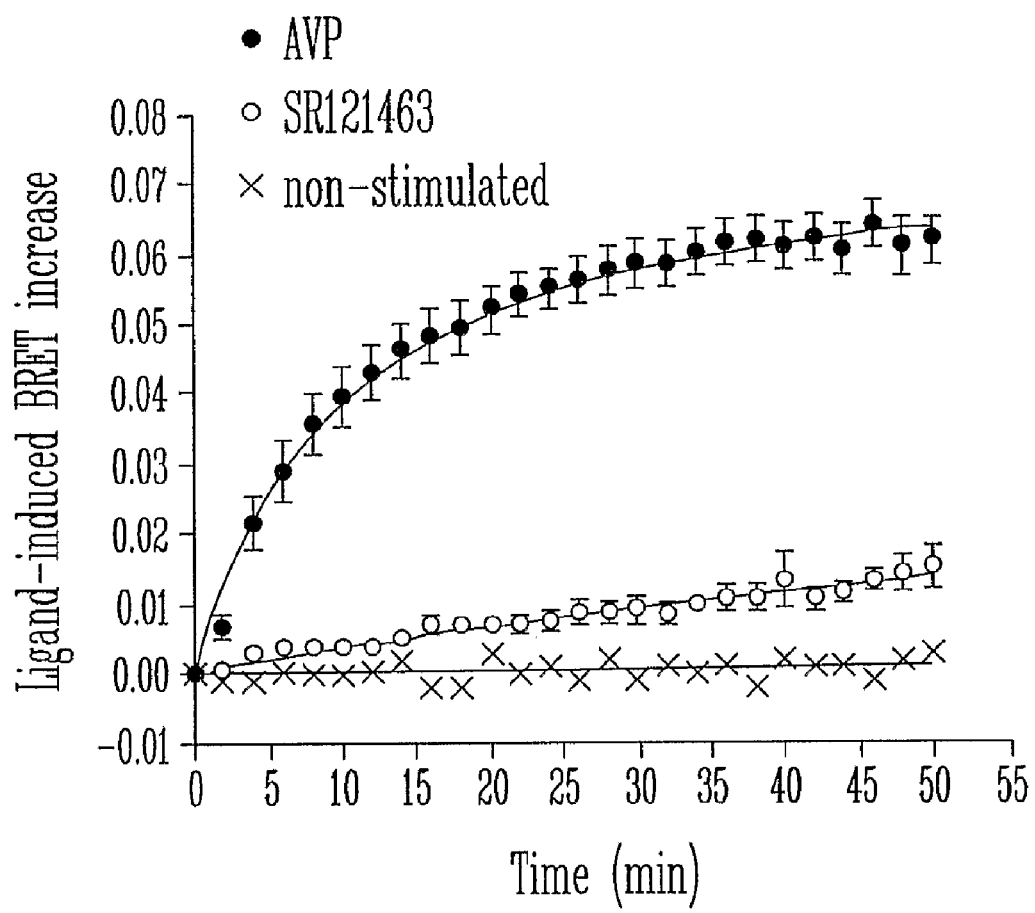
FIG_7

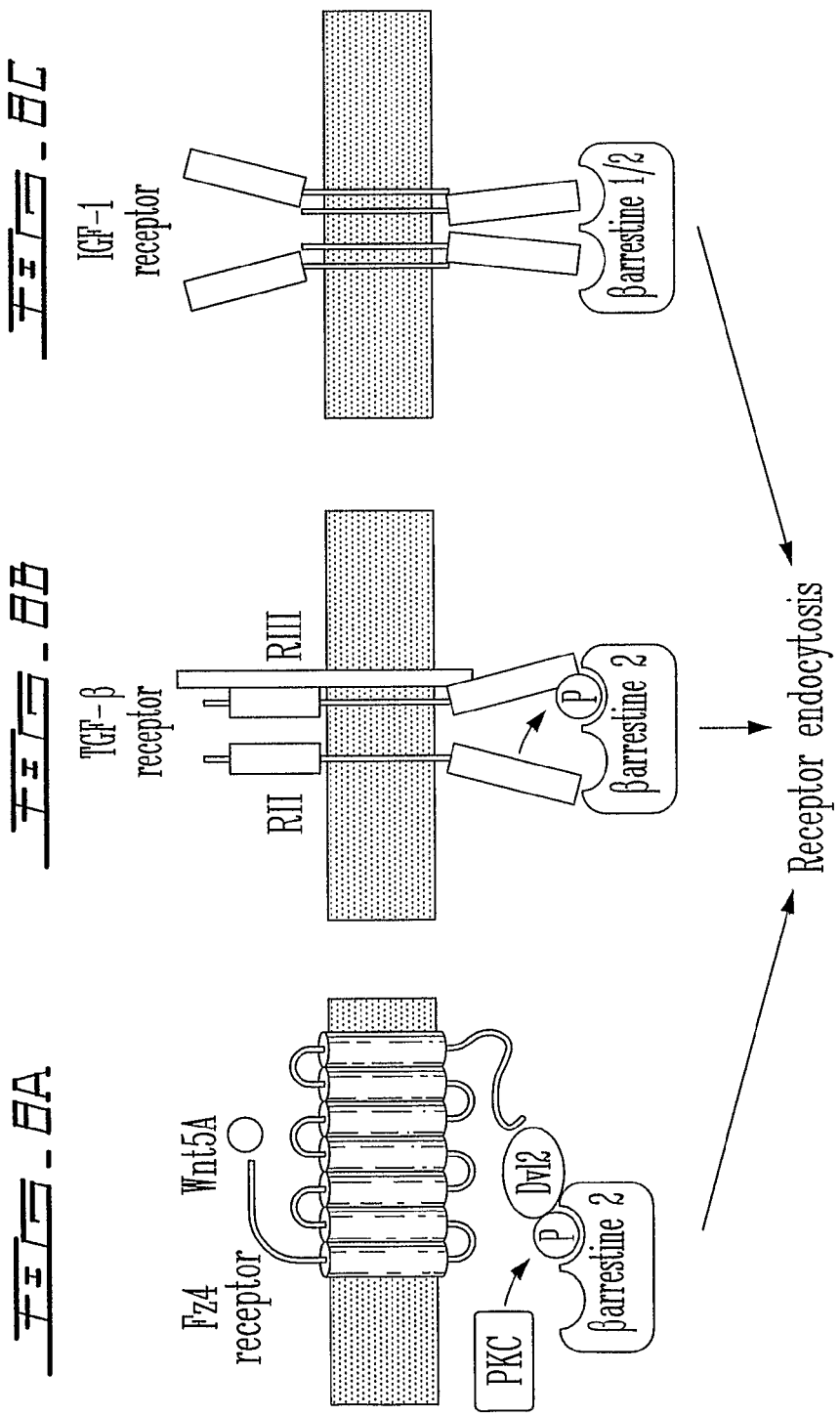

BRET2 βArrestin double-brilliance sensors of GPCR activation

Structure:

(SEQ ID NO:5)                          (SEQ ID NO:6)
BRET1 sensor: Rluc-GDLRRALENSHASAGYQACGTGS-βArrestin2-CLEDPRVPVAT-YFP
                        Linker1                              Linker2

(SEQ ID NO:7)       (SEQ ID NO:8)
BRET2 sensor: Acceptor-GSAGT-βArrestin1/2-KLPAT-RlucII
                    Linker3             Linker4 with Acceptor = {Ametrine; CFP; GFP$^{10}$}

Activation mechanism:

R = RlucII
G = GFP$^{10}$

FIG. 9C : βArrestin1 double-brilliance response upon AT1aR activation
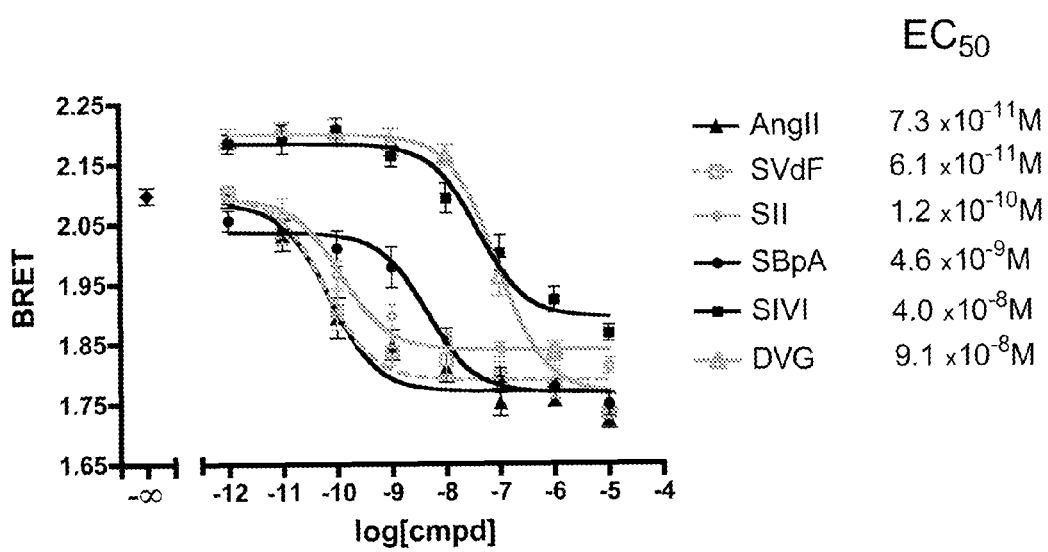
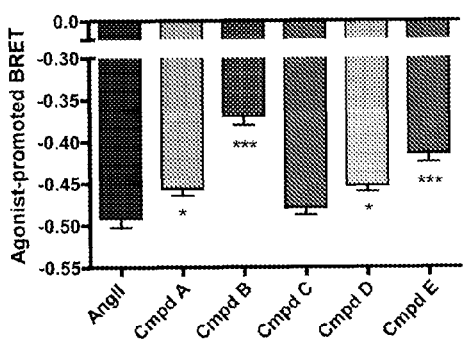

FIG. 10.
Z'-factor evaluation for βArrestin 1 and 2 db sensors
βArrestin2 db sensors
BRET1 sensor
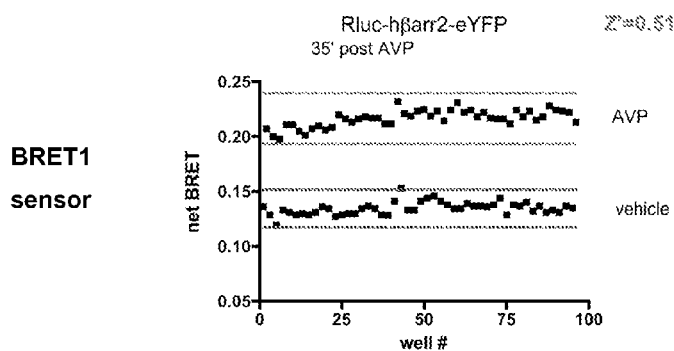
βArrestin1 db sensors  βArrestin2 db sensors
BRET2 sensors
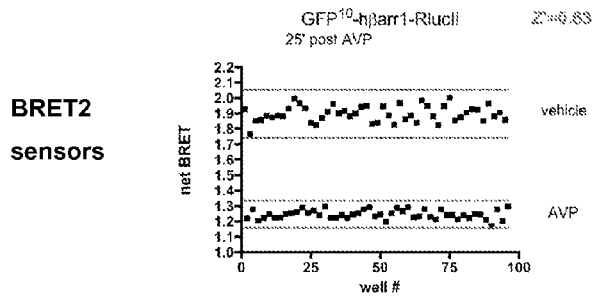 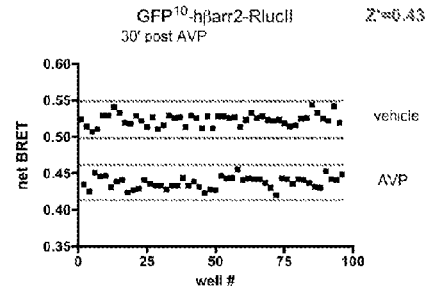

SEQUENCE LISTING

```
<160> NUMBER OF SEQ ID NOS: 11

<210> SEQ ID NO 1
<211> LENGTH: 1196
<212> TYPE: DNA
<213> ORGANISM: Renilla reniformis
<220> FEATURE:
<221> NAME/KEY: CDS
<222> LOCATION: (10)..(945)

<400> SEQUENCE: 1 agcttaaag atg act tcg aaa gtt tat gat cca gaa caa agg aaa cgg atg        51
          Met Thr Ser Lys Val Tyr Asp Pro Glu Gln Arg Lys Arg Met
            1               5                  10 ata act ggt ccg cag tgg tgg gcc aga tgt aaa caa atg aat gtt ctt         99
Ile Thr Gly Pro Gln Trp Trp Ala Arg Cys Lys Gln Met Asn Val Leu
 15                  20                  25                  30 gat tca ttt att aat tat tat gat tca gaa aaa cat gca gaa aat gct        147
Asp Ser Phe Ile Asn Tyr Tyr Asp Ser Glu Lys His Ala Glu Asn Ala
                 35                  40                  45 gtt att ttt tta cat ggt aac gcg gcc tct tct tat tta tgg cga cat        195
Val Ile Phe Leu His Gly Asn Ala Ala Ser Ser Tyr Leu Trp Arg His
             50                  55                  60 gtt gtg cca cat att gag cca gta gcg cgg tgt att ata cca gat ctt        243
Val Val Pro His Ile Glu Pro Val Ala Arg Cys Ile Ile Pro Asp Leu
         65                  70                  75 att ggt atg ggc aaa tca ggc aaa tct ggt aat ggt tct tat agg tta        291
Ile Gly Met Gly Lys Ser Gly Lys Ser Gly Asn Gly Ser Tyr Arg Leu
     80                  85                  90 ctt gat cat tac aaa tat ctt act gca tgg ttt gaa ctt ctt aat tta        339
Leu Asp His Tyr Lys Tyr Leu Thr Ala Trp Phe Glu Leu Leu Asn Leu
 95                 100                 105                 110 cca aag aag atc att ttt gtc ggc cat gat tgg ggt gct tgt ttg gca        387
Pro Lys Lys Ile Ile Phe Val Gly His Asp Trp Gly Ala Cys Leu Ala
                115                 120                 125 ttt cat tat agc tat gag cat caa gat aag atc aaa gca ata gtt cac        435
Phe His Tyr Ser Tyr Glu His Gln Asp Lys Ile Lys Ala Ile Val His
            130                 135                 140 gct gaa agt gta gta gat gtg att gaa tca tgg gat gaa tgg cct gat        483
Ala Glu Ser Val Val Asp Val Ile Glu Ser Trp Asp Glu Trp Pro Asp
        145                 150                 155 att gaa gaa gat att gcg ttg atc aaa tct gaa gaa gga gaa aaa atg        531
Ile Glu Glu Asp Ile Ala Leu Ile Lys Ser Glu Glu Gly Glu Lys Met
    160                 165                 170
```

```
gtt ttg gag aat aac ttc ttc gtg gaa acc atg ttg cca tca aaa atc    579
Val Leu Glu Asn Asn Phe Phe Val Glu Thr Met Leu Pro Ser Lys Ile
175             180                 185                 190 atg aga aag tta gaa cca gaa gaa ttt gca gca tat ctt gaa cca ttc    627
Met Arg Lys Leu Glu Pro Glu Glu Phe Ala Ala Tyr Leu Glu Pro Phe
                195                 200                 205 aaa gag aaa ggt gaa gtt cgt cgt cca aca tta tca tgg cct cgt gaa    675
Lys Glu Lys Gly Glu Val Arg Arg Pro Thr Leu Ser Trp Pro Arg Glu
            210                 215                 220 atc ccg tta gta aaa ggt ggt aaa cct gac gtt gta caa att gtt agg    723
Ile Pro Leu Val Lys Gly Gly Lys Pro Asp Val Val Gln Ile Val Arg
        225                 230                 235 aat tat aat gct tat cta cgt gca agt gat gat tta cca aaa atg ttt    771
Asn Tyr Asn Ala Tyr Leu Arg Ala Ser Asp Asp Leu Pro Lys Met Phe
    240                 245                 250 att gaa tcg gat cca gga ttc ttt tcc aat gct att gtt gaa ggc gcc    819
Ile Glu Ser Asp Pro Gly Phe Phe Ser Asn Ala Ile Val Glu Gly Ala
255                 260                 265                 270 aag aag ttt cct aat act gaa ttt gtc aaa gta aaa ggt ctt cat ttt    867
Lys Lys Phe Pro Asn Thr Glu Phe Val Lys Val Lys Gly Leu His Phe
                275                 280                 285 tcg caa gaa gat gca cct gat gaa atg gga aaa tat atc aaa tcg ttc    915
Ser Gln Glu Asp Ala Pro Asp Glu Met Gly Lys Tyr Ile Lys Ser Phe
            290                 295                 300 gtt gag cga gtt ctc aaa aat gaa caa taa ttactttggt tttttattta     965
Val Glu Arg Val Leu Lys Asn Glu Gln
        305                 310 cattttccc gggtttaata atataaatgt cattttcaac aatttatttt taactgaata  1025
tttcacaggg aacattcata tatgttgatt aatttagctc gaactttact ctgtcatatc 1085 attttggaat attcctcctt tcaatgaaac tttataaaca gtggttcaat taattaatat 1145 atattataat tacatttgtt atgtaataaa ctcggtttta ttataaaaaa a          1196

<210> SEQ ID NO 2
<211> LENGTH: 311
<212> TYPE: PRT
<213> ORGANISM: Renilla reniformis

<400> SEQUENCE: 2

Met Thr Ser Lys Val Tyr Asp Pro Glu Gln Arg Lys Arg Met Ile Thr
1               5                   10                  15

Gly Pro Gln Trp Trp Ala Arg Cys Lys Gln Met Asn Val Leu Asp Ser
            20                  25                  30

Phe Ile Asn Tyr Tyr Asp Ser Glu Lys His Ala Glu Asn Ala Val Ile
        35                  40                  45

Phe Leu His Gly Asn Ala Ala Ser Ser Tyr Leu Trp Arg His Val Val
    50                  55                  60

Pro His Ile Glu Pro Val Ala Arg Cys Ile Ile Pro Asp Leu Ile Gly
65                  70                  75                  80

Met Gly Lys Ser Gly Lys Ser Gly Asn Gly Ser Tyr Arg Leu Leu Asp
                85                  90                  95

His Tyr Lys Tyr Leu Thr Ala Trp Phe Glu Leu Leu Asn Leu Pro Lys
            100                 105                 110

Lys Ile Ile Phe Val Gly His Asp Trp Gly Ala Cys Leu Ala Phe His
        115                 120                 125

Tyr Ser Tyr Glu His Gln Asp Lys Ile Lys Ala Ile Val His Ala Glu
    130                 135                 140
```

```
Ser Val Val Asp Val Ile Glu Ser Trp Asp Glu Trp Pro Asp Ile Glu
145                 150                 155                 160

Glu Asp Ile Ala Leu Ile Lys Ser Glu Glu Gly Glu Lys Met Val Leu
                165                 170                 175

Glu Asn Asn Phe Phe Val Glu Thr Met Leu Pro Ser Lys Ile Met Arg
            180                 185                 190

Lys Leu Glu Pro Glu Glu Phe Ala Ala Tyr Leu Glu Pro Phe Lys Glu
                195                 200                 205

Lys Gly Glu Val Arg Arg Pro Thr Leu Ser Trp Pro Arg Glu Ile Pro
        210                 215                 220

Leu Val Lys Gly Gly Lys Pro Asp Val Val Gln Ile Val Arg Asn Tyr
225                 230                 235                 240

Asn Ala Tyr Leu Arg Ala Ser Asp Asp Leu Pro Lys Met Phe Ile Glu
                245                 250                 255

Ser Asp Pro Gly Phe Phe Ser Asn Ala Ile Val Glu Gly Ala Lys Lys
            260                 265                 270

Phe Pro Asn Thr Glu Phe Val Lys Val Lys Gly Leu His Phe Ser Gln
        275                 280                 285

Glu Asp Ala Pro Asp Glu Met Gly Lys Tyr Ile Lys Ser Phe Val Glu
    290                 295                 300

Arg Val Leu Lys Asn Glu Gln
305                 310

<210> SEQ ID NO 3
<211> LENGTH: 311
<212> TYPE: PRT
<213> ORGANISM: Renilla reniformis

<400> SEQUENCE: 3

Met Thr Ser Lys Val Tyr Asp Pro Glu Gln Arg Lys Arg Met Ile Thr
1               5                   10                  15

Gly Pro Gln Trp Trp Ala Arg Cys Lys Gln Met Asn Val Leu Asp Ser
                20                  25                  30

Phe Ile Asn Tyr Tyr Asp Ser Glu Lys His Ala Glu Asn Ala Val Ile
            35                  40                  45

Phe Leu His Gly Asn Ala Thr Ser Ser Tyr Leu Trp Arg His Val Val
        50                  55                  60

Pro His Ile Glu Pro Val Ala Arg Cys Ile Ile Pro Asp Leu Ile Gly
65                  70                  75                  80

Met Gly Lys Ser Gly Lys Ser Gly Asn Gly Ser Tyr Arg Leu Leu Asp
                85                  90                  95

His Tyr Lys Tyr Leu Thr Ala Trp Phe Glu Leu Leu Asn Leu Pro Lys
            100                 105                 110

Lys Ile Ile Phe Val Gly His Asp Trp Gly Ala Ala Leu Ala Phe His
        115                 120                 125

Tyr Ser Tyr Glu His Gln Asp Lys Ile Lys Ala Ile Val His Ala Glu
130                 135                 140

Ser Val Val Asp Val Ile Glu Ser Trp Asp Glu Trp Pro Asp Ile Glu
145                 150                 155                 160

Glu Asp Ile Ala Leu Ile Lys Ser Glu Glu Gly Glu Lys Met Val Leu
                165                 170                 175

Glu Asn Asn Phe Phe Val Glu Thr Val Leu Pro Ser Lys Ile Met Arg
            180                 185                 190

Lys Leu Glu Pro Glu Glu Phe Ala Ala Tyr Leu Glu Pro Phe Lys Glu
```

```
              195                 200                 205
Lys Gly Glu Val Arg Arg Pro Thr Leu Ser Trp Pro Arg Glu Ile Pro
            210                 215                 220

Leu Val Lys Gly Gly Lys Pro Asp Val Val Gln Ile Val Arg Asn Tyr
225                 230                 235                 240

Asn Ala Tyr Leu Arg Ala Ser Asp Asp Leu Pro Lys Met Phe Ile Glu
                245                 250                 255

Ser Asp Pro Gly Phe Phe Ser Asn Ala Ile Val Glu Gly Ala Lys Lys
            260                 265                 270

Phe Pro Asn Thr Glu Phe Val Lys Val Lys Gly Leu His Phe Ser Gln
            275                 280                 285

Glu Asp Ala Pro Asp Glu Met Gly Lys Tyr Ile Lys Ser Phe Val Glu
290                 295                 300

Arg Val Leu Lys Asn Glu Gln
305                 310

<210> SEQ ID NO 4
<211> LENGTH: 312
<212> TYPE: PRT
<213> ORGANISM: Renilla reniformis

<400> SEQUENCE: 4

Met Ala Ser Lys Val Tyr Asp Pro Glu Gln Arg Lys Arg Met Ile Thr
1               5                   10                  15

Gly Pro Gln Val Val Trp Ala Arg Cys Lys Gln Met Asn Val Leu Asp
            20                  25                  30

Ser Phe Ile Asn Tyr Tyr Asp Ser Glu Lys His Ala Glu Asn Ala Val
            35                  40                  45

Ile Phe Leu His Gly Asn Ala Thr Ser Ser Tyr Leu Trp Arg His Val
        50                  55                  60

Val Pro His Ile Glu Pro Val Ala Arg Cys Ile Ile Pro Asp Leu Ile
65                  70                  75                  80

Gly Met Gly Lys Ser Gly Lys Ser Gly Asn Gly Ser Tyr Arg Leu Leu
                85                  90                  95

Asp His Tyr Lys Tyr Leu Thr Ala Trp Phe Glu Leu Leu Asn Leu Pro
            100                 105                 110

Lys Lys Ile Ile Phe Val Gly His Asp Trp Gly Ala Ala Leu Ala Phe
            115                 120                 125

His Tyr Ala Tyr Glu His Gln Asp Arg Ile Lys Ala Ile Val His Met
        130                 135                 140

Glu Ser Val Val Asp Val Ile Glu Ser Trp Asp Glu Trp Pro Asp Ile
145                 150                 155                 160

Glu Glu Asp Ile Ala Leu Ile Lys Ser Glu Glu Gly Glu Lys Met Val
                165                 170                 175

Leu Glu Asn Asn Phe Phe Val Glu Thr Val Leu Pro Ser Lys Ile Met
            180                 185                 190

Arg Lys Leu Glu Pro Glu Glu Phe Ala Ala Tyr Leu Glu Pro Phe Lys
            195                 200                 205

Glu Lys Gly Glu Val Arg Arg Pro Thr Leu Ser Trp Pro Arg Glu Ile
        210                 215                 220

Pro Leu Val Lys Gly Gly Lys Pro Asp Val Val Gln Ile Val Arg Asn
225                 230                 235                 240

Tyr Asn Ala Tyr Leu Arg Ala Ser Asp Asp Leu Pro Lys Leu Phe Ile
                245                 250                 255
```

```
Glu Ser Asp Pro Gly Phe Phe Ser Asn Ala Ile Val Glu Gly Ala Lys
            260                 265                 270

Lys Phe Pro Asn Thr Glu Phe Val Lys Val Lys Gly Leu His Phe Leu
        275                 280                 285

Gln Glu Asp Ala Pro Asp Glu Met Gly Lys Tyr Ile Lys Ser Phe Val
    290                 295                 300

Glu Arg Val Leu Lys Asn Glu Gln
305                 310

<210> SEQ ID NO 5
<211> LENGTH: 23
<212> TYPE: PRT
<213> ORGANISM: Artificial Sequence
<220> FEATURE:
<223> OTHER INFORMATION: Synthetic linker

<400> SEQUENCE: 5

Gly Asp Leu Arg Arg Ala Leu Glu Asn Ser His Ala Ser Ala Gly Tyr
1               5                   10                  15

Gln Ala Cys Gly Thr Gly Ser
            20

<210> SEQ ID NO 6
<211> LENGTH: 11
<212> TYPE: PRT
<213> ORGANISM: Artificial Sequence
<220> FEATURE:
<223> OTHER INFORMATION: Synthetic linker

<400> SEQUENCE: 6

Cys Leu Glu Asp Pro Arg Val Pro Val Ala Thr
1               5                   10

<210> SEQ ID NO 7
<211> LENGTH: 5
<212> TYPE: PRT
<213> ORGANISM: Artificial Sequence
<220> FEATURE:
<223> OTHER INFORMATION: Synthetic linker

<400> SEQUENCE: 7

Gly Ser Ala Gly Thr
1               5

<210> SEQ ID NO 8
<211> LENGTH: 5
<212> TYPE: PRT
<213> ORGANISM: Artificial Sequence
<220> FEATURE:
<223> OTHER INFORMATION: Synthetic linker

<400> SEQUENCE: 8

Lys Leu Pro Ala Thr
1               5

<210> SEQ ID NO 9
<211> LENGTH: 15
<212> TYPE: PRT
<213> ORGANISM: Artificial Sequence
<220> FEATURE:
<223> OTHER INFORMATION: Synthetic linker

<400> SEQUENCE: 9

Gly Ser Ala Gly Thr Gly Ser Ala Gly Thr Gly Ser Ala Gly Thr
1               5                   10                  15
```

```
<210> SEQ ID NO 10
<211> LENGTH: 15
<212> TYPE: PRT
<213> ORGANISM: Artificial Sequence
<220> FEATURE:
<223> OTHER INFORMATION: Synthetic peptide

<400> SEQUENCE: 10

Lys Leu Pro Ala Thr Lys Leu Pro Ala Thr Lys Leu Pro Ala Thr
1               5                   10                  15

<210> SEQ ID NO 11
<211> LENGTH: 16
<212> TYPE: PRT
<213> ORGANISM: Artificial Sequence
<220> FEATURE:
<223> OTHER INFORMATION: Synthetic linker

<400> SEQUENCE: 11

Arg Glu Ala Ala Ala Arg Glu Ala Ala Ala Arg Glu Ala Ala Ala Arg
1               5                   10                  15
```

ARRESTIN BIOSENSOR

This application is a Continuation-in-Part of U.S. application Ser. No. 11/579,482 filed Nov. 3, 2006, now U.S. Pat. No. 7,932,080, which is a national stage entry of PCT/CA2005/00695 filed on May 4, 2005 which claims benefit of 60/567,454 filed May 4, 2004, all incorporated by reference herein.

TECHNICAL FIELD

The invention relates to a novel biosensor and method suitable for monitoring activation of receptors and signaling molecules. More specifically, the invention concerns the use of a modified arrestin as a biosensor to monitor the activation state of receptors, such as G protein-coupled receptors (GPCR). Advantageously, the biosensor and method of the present invention allow for a highly sensitive and quantitative assay that can be used in large-scale screening analyses.

BACKGROUND OF THE INVENTION

The largest class of cell surface receptors in mammalian genomes is the superfamily of G protein-coupled receptors (GPCRs). GPCRs are proteins that span the membrane of a cell and relay the information provided by numerous ligands, e.g. hormones and neurotransmitters, into intracellular signalling pathways. GPCRs are thus the targets of many clinically important drugs, with approximately half of all current prescription drugs acting through GPCRs (Drews J (1996) Genomic sciences and the medicine of tomorrow. Nat Biotechnol 14: 1516-1518). Examples of GPCRs are many and include beta-2 adrenergic receptor (β2-AR), Frizzled 4 (Fz4), V2-vasopressin receptor (V2R), V1a vasopressin receptor (V1aR), δ-opioid receptor (δ-OR), platelet-activating factor receptor (PAFR), CC chemokine receptor type 5 (CCR5), and angiotensin receptor type 1a (AT1aR).

GRCRs relay the information encoded by the ligand (e.g. hormones and neurotransmitters) through the activation of G proteins and intracellular effector molecules. G proteins are heterotrimeric proteins, consisting of an alpha, a beta, and a gamma subunit. The three G-subunits are non-covalently bound together and the G protein as a whole binds to the inside surface of the cell membrane and associates with the GPCR. Starting in such conformation, the G-alpha subunit is complexed to GDP (guanosine diphosphate). When a ligand binds to a domain of the GPCR accessible from the outside of the cell membrane, a conformational change in the GPCR occurs, which in turn prompts the exchange of the GDP for a molecule of guanosine triphosphoate (GTP) on the G-alpha subunit, and activates the G-protein. The G-protein's α subunit, together with the bound GTP, can then dissociate from the β and γ subunits to further affect intracellular signaling proteins or target functional proteins directly, depending on the α subunit type (e.g. Gαs, Gαi/o, Gαq/11, Gα12/13).

In order to turn off this response by GPCRs to stimulus, or adapt to a persistent stimulus, the activated GPCRs are inactivated. This inactivation may be achieved, in part, by the binding of a soluble protein, β-arrestin (β-arr), which uncouples the receptor from the downstream G protein after the receptor is phosphorylated by a G protein-coupled receptor kinase (GRK). More specifically, through their binding to agonist-occupied, GRK-phosphorylated receptors, β-arrs prevent further coupling to G proteins and promote GPCR endocytosis, thus leading to decreased signalling efficacy.

Despite our growing understanding of the diversity in GPCR signaling mechanisms, drug efficacy is often defined only in terms of the regulation of the classical G protein signaling. Within this framework, agonists are defined as drugs that stabilize an active receptor conformation that induces G protein activation, whereas inverse agonists favor an inactive receptor state that reduces spontaneous G protein signaling. The question arises as to whether this paradigm may be transferred to drug effects generated through the formation of metastable complexes involving scaffolding proteins such as β-arr. Because all studies describing β-arr-mediated MAPK signalling have concentrated on agonist drugs, little is known of how ligands that are commonly classified as inverse agonists may regulate the scaffold assembly that is crucial for such signalling.

In one study (Azzi et al, 2003), this question was addressed by assessing whether β-adrenergic receptor (β2AR) and V2 vasopressin receptor (V2R) ligands with proven inverse efficacy on adenylyl cyclase (AC) activity could also regulate MAPK activation via receptor-mediated scaffold formation. It was found that, despite being inverse agonists in the AC pathway, the β2AR (ICI118551 and propranolol) and V2R (SR121463A) induced the recruitment of β-arr leading to the activation of the ERK cascade. Such observations indicate that the same drug acting on a unique receptor can have opposite efficacies depending on the signaling pathway considered.

The above study relied on the use of a bimolecular bioluminescence resonance energy transfer (BRET) assay. It was used to assess β-arrestin recruitment to β2AR or V2R. Fusion proteins consisting of GFP10 variant (GFP) covalently attached to the carboxyl tail of the receptor of interest (β2AR-GFP; V2R-GFP) were co-expressed with β-arrestin 2 fused at its carboxyl terminus to Rluc (β-arrestin-Rluc). After incubation of the transfected cells with different ligands, coelenterazine 400a (Perkin-Elmer, Wellesley, Mass., USA) was added and readings were collected using a modified top-count apparatus (BRETCount, Packard) that allows the sequential integration of the signals detected at 370-450 nm and 500-530 nm. The BRET signal was determined by calculating the ratio of the light emitted by the Receptor-GFP (500-530 nm) over the light emitted by the β-arrestin2-Rluc (370-450 nm). The values were corrected by subtracting the background signal detected when the β-arrestin2-Rluc construct was expressed alone.

While the results elicited from the above study were instructive, a necessary feature involved the construction of fusion proteins that included the receptors of interest. Ideally, a method could be devised in which receptor activation might be observed without first having to modify the receptors that are to be studied. Other features of such a method that would make it highly desirable for research and development endeavors include the following: (1) a high level of sensitivity; (2) an ability to provide quantitative results; (3) adaptability for use in large scale screening analyses; (4) an assay that requires the expression of a single recombinant construct; and (5) a biosensor based on an intramolecular RET signal.

Resonance energy transfer (abbreviated RET, and also referred to as Förster resonance energy transfer), is a mechanism describing energy transfer between two chromophores, having overlapping emission/absoprtion spectra. When the two chromophores (the "donor" and the "acceptor"), are within 10-100 Å of one another and their transition dipoles are appropriately oriented, the donor chromophore is able to transfer its excited-state energy to the acceptor chromophore through nonradiative dipole-dipole coupling. When both chromophores are fluorescent, the term typically used is "fluorescence resonance energy transfer" (abbreviated FRET). In bioluminescence resonance energy transfer (BRET), the donor chromophore of the RET pair, rather than being a fluorophore, is a bioluminescent molecule, typically luciferase. In the presence of a substrate, bioluminescence from the donor excites the acceptor fluorophore through the same Förster resonance energy transfer mechanism described above (Xu, Y. et al., PNAS, 96:151-156 (1999)).

There is a need for a simpler method to measure receptor activity in living cells. The present invention seeks to meet this and related needs.

SUMMARY OF THE INVENTION

In accordance with the present invention, a resonance energy transfer (RET) biosensor comprising an arrestin tagged with a first and a second chromophore, wherein said first chromophore is a fluorophore and said second chromophore is a fluorophore or a bioluminophore, is provided.

Other objects, advantages and features of the present invention will become more apparent upon reading of the following non-restrictive description of preferred embodiments thereof, given by way of example only with reference to the accompanying figures.

BRIEF DESCRIPTION OF THE FIGURES

FIG. 1: Double-brilliance β-arr. Schematic diagram illustrating how agonist-promoted conformational rearrangement of β-arr can be measured as changes in BRET using double-brilliance β-arr. Luc and YFP are represented by cylinders proportional to their sizes, but their real orientation is unknown.

FIG. 6: Agonist-promoted conformational change of constitutively activated βarrestin mutants. HEK293 cells were transfected with V2R and either Luc-βarr-YFP or Luc-βarr (3A)-YFP or Luc-βarr (IV)-YFP. Cells were stimulated or not for 10 min with 1 μM AVP prior to the addition of 5 μM coelenterazine h and performing the BRET measurements as described in the previous figure. Inset, AVP-induced BRET increase. The BRET signal was determined by calculating the ratio of the light emitted by YFP over the light emitted by Luc following the addition of coelenterazine h. The values were corrected by subtracting the background BRET signals detected when Luc-βarr was expressed alone. Data represent the mean±SEM of two independent experiments. * indicates p<0.05 between treatment and each individual control condition.

FIG. 7: Conformational change of βarrestin induced by ligands of different efficacies. HEK293 cells transiently co-expressing the V2R and Luc-βarr-YFP were subjected to real-time BRET measurements in the presence or absence of two different V2R ligands. The basal BRET signals were subtracted from each condition to express the data as ligand-induced BRET increase. The figure shows the detection of conformational changes of Luc-βarr-YFP in time, reflected by the increase in BRET signal, as induced by the V2R agonist AVP or the inverse agonist SR121463. No BRET increase was observed when cells were incubated in the presence of the carrier alone (non-stimulated). The fact that the observed increase in BRET signal induced by SR121463 is significantly lower than that induced by AVP treatment can be correlated with the smaller SR121463-mediated recruitment of βarrestin to the V2R when compared to AVP, as reported previously (Azzi et al, 2003).

FIG. 8: βarrestin-dependant endocytosis beyond GPCRs. (A) Endocytosis of the receptor Frizzled 4 (Fz4) stimulated by Wnt5a is orchestrated by βarrestin 2, in a manner that is dependent upon the phosphorylation of the adaptor protein Dishevelled 2 (Dvl2) by protein kinase C (PKC). (B) Endocytosis of the RII and RIII receptor subtypes of TGF-β1 is orchestrated by βarrestin 2, and facilitated by the phosphorylation of RIII by RII. (C) Endocytosis of the IGF1 receptor is orchestrated by βarrestin (Modified from Lefkowitz & Whalen, 2004.).

FIG. 10: Z'-factor evaluation for both BRET1- and BRET2-βArrestin sensors. HEK293 cells transiently expressing both V2R and the double-brilliance sensor, were exposed to either 100 nM AVP or a control vehicle, for 25-35 min. BRET ratios are represented for each individual well of a 96-well plate. Z'-factors were calculated as described in (Ji-Hu Zhang et al. 1999 J Biomol Screen, 4; 67). A Z'-factor between 0.4 and 1 is considered a robust assay.

DETAILED DESCRIPTION OF THE INVENTION

Definitions

Figure 2A:
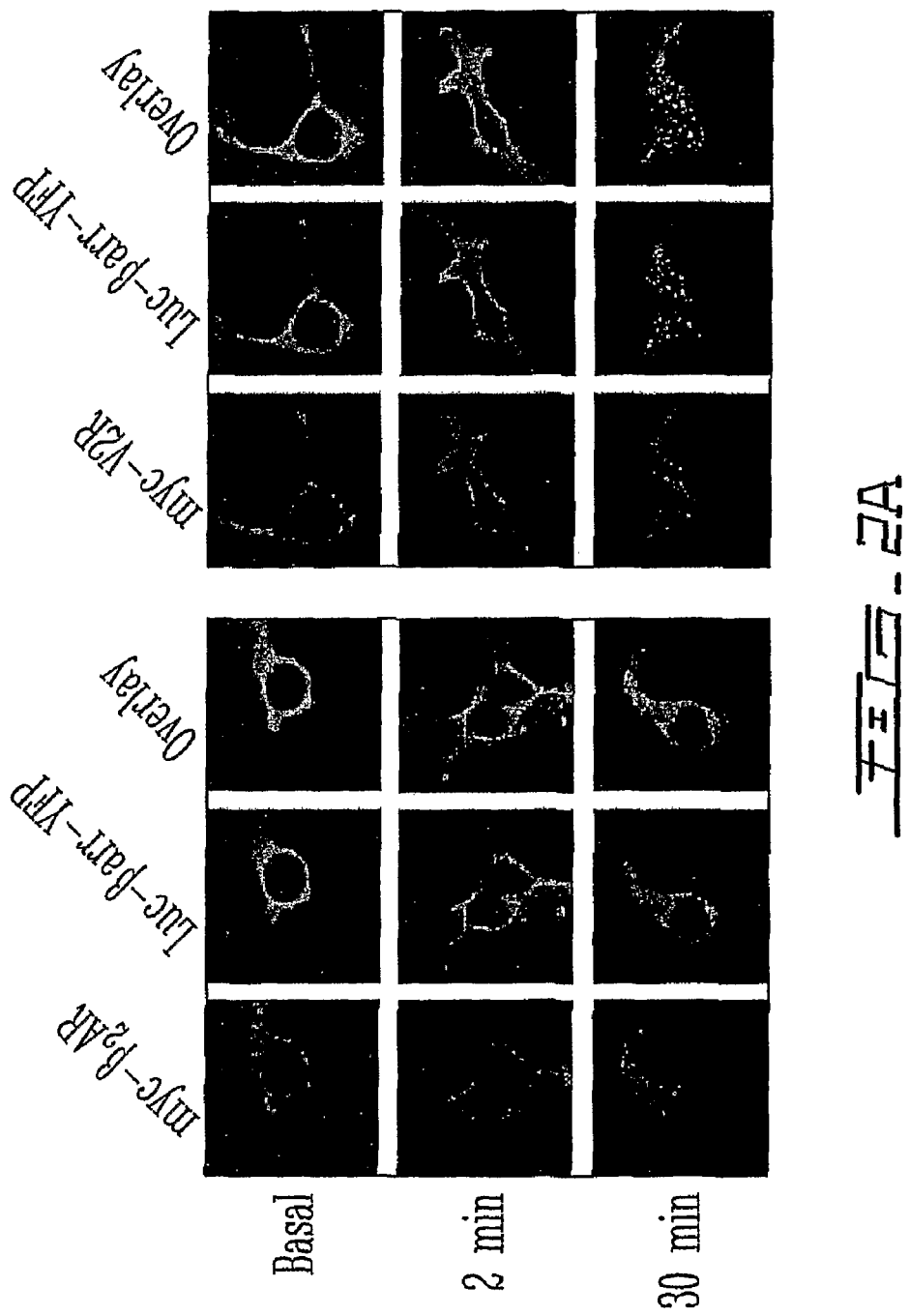
FIG. 2: Functionality of double-brilliance β-arr. HEK293 (A-C) or COS (D) cells were transiently transfected with the indicated plasmids. (A) Cells incubated or not in the presence of saturating concentrations of specific agonists (β2-AR, 10 mM isoproterenol (ISO); V2R, 1 mM arginine vasopressin (AVP)). Localization of Luc-β-arr-YFP and Myc-tagged receptors was analysed by confocal fluorescence microscopy. (B) Agonist-induced recruitment of β-arr measured using intermolecular BRET2. t½=half-time of maximal β-arr recruitment. (C) Dose-dependent recruitment of β-arr to the receptors measured in intermolecular BRET2 following 2 min stimulation with the agonist. EC50=concentration of agonist producing half-maximal β-arr recruitment. (D) Cells treated or not for 15 min with the specific agonists at 37° C. and cell-surface receptor levels measured by enzyme-linked immunosorbent assay (ELISA). Receptor endocytosis is defined as the loss of cell-surface immunoreactivity and is expressed as a percentage of total immunoreactivity measured under basal conditions. Expression levels of β-arr were controlled using western blot (data not shown). Data are the mean±s.e.m. of at least three independent experiments. *P<0.05 between treatment and each individual control condition. Mock, non-transfected cells.

Unless otherwise defined, the terms used in the present description have the meanings that would be understood by a person of skill in the art.

Ligand: A molecule which may be but is not restricted to a hormone, neurotransmitor, chemical compound, drug, or diagnostic agent that binds to a receptor and has an agonistic, inverse agonistic, antagonistic or allosteric effect on the receptor. Ligands may be further classified as follows (for a more detailed summary, see Wilson, Keith et al. (Eds.), Principles and Techniques of Biochemistry and Molecular Biology, 7th Edition (2010), Chapter 17, incorporated by reference herein):

a) Agonist: a ligand that has the same or similar effect as a hormone, neurotransmitter or signaling molecule or a group of hormones, neurotransmitters or signaling molecules activating a receptor, by binding to the same natural receptor. A partial agonist is a type of agonist that with lower intrinsic activity than a full agonist and that produces a lower maximum effect. Examples of agonists include:
  i. Angiotensin II: The active form of angiotensin. An octapeptide found in blood, it is synthesised from angiotensin I and quickly destroyed. Angiotensin II causes profound vasoconstriction with resulting increase in blood pressure. It is an agonist of the angiotensin receptor.
  ii. AVP: arginine vasopressin, vasopressin containing arginine, as that from most mammals, including man. This hormone controls water reabsorbtion by the kidney and is also known as the antidiuretic hormone.
  iii. ISO: isoproterenol, a synthetic beta-adrenergic receptor agonist which controls peripheral vasoconstriction, bronchodilation and increased cardiac rate, contractility and output.
  iv. SNC80: 4[(*R*)-α-((2S,5R)-4-allyl-2,5-dimethyl-1-piperazinyl)-3-methoxybenzyl]-N,N-diethylbenzamide. An agonist of the delta-opioid receptor that possesses anti-nociceptive action.
  v. PAF: platelet-activating factor; a hormone that regulates platelet aggregation. It is an agonist of the PAF receptor.
  vi. hRANTES: human RANTES (regulated upon activation, normal T cell expressed and secreted) is a chemoattractant for monocytes and T cells. It is an agonist of the chemokine receptors: CCR1, CCR3, CCR5 and GPR75.
  vii. Wnt5a: Ligand for members of the frizzled family of seven transmembrane receptors.
  viii. IGF1: insulin-like growth factor 1 (also known as somatomedin C), a hormone homologous to proinsulin.
  ix. TGF-β1: Transforming Growth Factor-beta1, a multifunctional peptide that controls proliferation, differentiation, and other functions in many cell types. Many cells synthesize TGF-beta 1 and essentially all of them have specific receptors for this peptide. TGF-beta 1 regulates the actions of many other peptidic growth factors and determines a positive or negative direction of their effects.

b) Inverse agonist: a ligand that produces an effect opposite to that of an agonist by occupying the same receptor. Examples include:

i. SR121463: SR121463 is a selective, orally active, non-peptide antagonist of vasopressin (AVP) V2 receptors, with powerful aquaretic properties in various animal species and humans. SR121463 also behaves as an inverse agonist in cells expressing constitutively active human V2 receptor.

c) Antagonist: a ligand that counteracts the effect of another ligand (agonist or inverse agonist) acting on a receptor by binding to the same receptor, thus blocking or dampening the ability of the agonist to bind (also called competitive antagonist). Neutral antagonists have affinity but no efficacy for their cognate receptors.

d) Allosteric regulator: a ligand that modulates receptor activity through binding at a site that is different from that bound by orthosteric ligands (i.e. endogenous ligands). Allosteric regulators may have an antagonistic or agonistic effect.

Chromophore: A small molecule, or a part of a larger molecule, that is responsible for the spectral band of the molecule.

Biosensor: A type of biomolecular probe that measures the presence or concentration of biological molecules, biological structures, activity state etc., by translating a biochemical interaction at the probe surface into a quantifiable physical signal such as light or electric pulse.

Receptor: A popular and generally accepted hypothesis that appears to explain many pharmacodynamic phenomena holds that specialized protein molecules on the surfaces of cells provide a "fit" for an intrinsic molecule (such as a hormone or neurotransmitter) or a drug such that when that molecule occupies (binds to) that area, it leads to a biochemical or physiologic response. This idea is often compared to the operation of a lock (receptor) by a key (ligand). Examples of GPCR receptors include:

a) $\beta_2$-AR: beta-2 adrenergic receptor
b) Frizzled 4 (Fz4): a seven transmembrane receptor that selectively recognizes hormones of the Wnt family.
c) V2R: Vasopressin V2 receptor
d) V1aR: Vasopressin V1a receptor
e) δ-OR: δ-opioid receptor
f) PAFR: platelet-activating factor receptor
g) CCR5: CC chemokine receptor type 5
h) AT1aR: angiotensin receptor type 1a Signalling molecule: a membrane or soluble protein involved in the transaction of signals in cells initiated by hormones, neurotransmitters or synthetic ligands.

Identity as known in the art, is a relationship between two or more polypeptide sequences, as determined by comparing the sequences. In the art, "identity" also means the degree of sequence relatedness between polypeptides as determined by the match between strings of such sequences. "Identity" and "similarity" can be readily calculated by known methods, including, but not limited to, those described in (Computational Molecular Biology, Lesk, A. M., Ed., Oxford University Press, New York, 1988; Biocomputing: Informatics and Genome Projects, Smith, D. W., Ed., Academic Press, New York, 1993; Computer Analysis of Sequence Data, Part I, Griffin, A. M., and Griffin, H. G., Eds., Humana Press, New Jersey, 1994; Sequence Analysis in Molecular Biology, von Heinje, G., Academic Press, 1987; and Sequence Analysis Primer, Gribskov, M. and Devereux, J., Eds., M Stockton Press, New York, 1991; and Carillo, H., and Lipman, D., SIAM J Applied Math., 48: 1073 (1988).

By way of example, a polypeptide sequence may be identical to the reference sequence, that is be 100% identical, or it may include up to a certain integer number of amino acid residue alterations as compared to the reference sequence such that the % identity is less than 100%. Such alterations are selected from: at least one conservative or non-conservative amino acid residue substitution, deletion, or insertion, and wherein said alterations may occur at the amino- or carboxy-terminal positions of the reference polypeptide sequence or anywhere between those terminal positions, interspersed either individually among the amino acid residues in the reference sequence or in one or more contiguous groups within the reference sequence. The number of amino acid residue alterations for a given % identity is determined by multiplying the total number of amino acids in the reference polypeptide by the numerical percent of the respective percent identity (divided by 100) and then subtracting that product from said total number of amino acids in the reference polypeptide.

Conservative amino acid variants can also comprise non-naturally occurring amino acid residues. Non-naturally occurring amino acids include, without limitation, trans-3-methylproline, 2,4-methanoproline, cis-4-hydroxyproline, trans-4-hydroxyproline, N-methyl-glycine, allothreonine, methylthreonine, hydroxy-ethylcysteine, hydroxyethylhomocysteine, nitro-glutamine, homoglutamine, pipecolic acid, thiazolidine carboxylic acid, dehydroproline, 3- and 4-methylproline, 3,3-dimethylproline, tert-leucine, norvaline, 2-azaphenyl-alanine, 3-azaphenylalanine, 4-azaphenylalanine, and 4-fluorophenylalanine. Several methods are known in the art for incorporating non-naturally occurring amino acid residues into proteins. For example, an in vitro system can be employed wherein nonsense mutations are suppressed using chemically aminoacylated suppressor tRNAs. Methods for synthesizing amino acids and aminoacylating tRNA are known in the art. Transcription and translation of plasmids containing nonsense mutations is carried out in a cell-free system comprising an E. coli S30 extract and commercially available enzymes and other reagents. Proteins are purified by chromatography. (Robertson, et al., J. Am. Chem. Soc, 113: 2722,1991; Ellman, et al., Methods Enzymol, 202: 301, 1991; Chung, et al., Science, 259: 806-9, 1993; and Chung, et al, Proc. Natl. Acad. Sci. USA, 90: 10145-9, 1993). In a second method, translation is carried out in Xenopus oocytes by microinjection of mutated mRNA and chemically aminoacylated suppressor tRNAs (Turcatti, et al, J. Biol. Chem., 271: 19991-8, 1996). Within a third method, E. coli cells are cultured in the absence of a natural amino acid that is to be replaced (e.g., phenylalanine) and in the presence of the desired non-naturally occurring amino acid(s) (e.g., 2-azaphenylalanine, 3-azaphenylalanine, 4-azaphenylalanine, or 4-fluorophenylalanine). The non-naturally occurring amino acid is incorporated into the protein in place of its natural counterpart. (Koide, et al, Biochem., 33: 7470-6, 1994). Naturally occurring amino acid residues can be converted to non-naturally occurring species by in vitro chemical modification. Chemical modification can be combined with site-directed mutagenesis to further expand the range of substitutions (Wynn, et al. Protein Sci., 2: 395-403, 1993).

Variant: refers to a polypeptide or polynucleotide that differs from a reference polypeptide or polynucleotide, but retains essential properties. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more modifications (e.g., substitutions, additions, and/or deletions). A variant of a polypeptide includes conservatively modified variants. A substituted or inserted amino acid residue may or may not be one encoded by the genetic code. A variant of a polypeptide may be naturally occurring, such as an allelic variant, or it may be a variant that is not known to occur naturally.

Modifications and changes can be made in the structure of the polypeptides of this disclosure and still obtain a molecule having similar characteristics as the polypeptide (e.g., a conservative amino acid substitution). For example, certain amino acids can be substituted for other amino acids in a sequence without appreciable loss of activity. Because it is the interactive capacity and nature of a polypeptide that defines that polypeptide's biological functional activity, certain amino acid residue substitutions can be made in a polypeptide sequence and nevertheless obtain a polypeptide with like properties.

In one aspect, such variants have at least 60%, at least 70%, at least 80%, at least 85%, at least 90%, at least 91, at least 92%, at least 93%, at least 94%, at least 95%, at least 96%, at least 97%, at least 98%, or at least 99% sequence identity with the reference polypeptide or polynucleotide.

Arrestin:

A receptor could either be constitutively active or inactive and, ligands such agonists, inverse agonists and allosteric modulators are known to modulate this activity. The interaction of arrestins, including β-arrestin (βarr), with receptors, such as but not limited to GPCRs, is a reflection of the receptor activity. The beta-arrestins belong to the family of arrestins. It is generally accepted that there are 4 arrestins in mammals: arrestins 1-4. Arrestin-1 and arrestin-4 are visual arrestins whereas arrestin-2 and arrestin-3 are widely distributed in all tissues and correspond to beta-arrestin-1 and beta-arrestin-2 respectively. The interaction of β-arrestins with receptors or other proteins, such as a beta2-adaptin, has an impact on the conformation of the β-arrestins. This change in conformation is linked to its property of interacting with effectors of signaling pathways and receptor endocytosis. This characteristic of arrestin is conserved throughout evolution of eukaryotic organisms and, is the basis for the unimolecular RET-based conformational sensors: β-arrestin1 (also known as Arrestin-2 or β-arrestin) and β-arrestin 2 (also known as Arrestin-3) double brilliance sensors to monitor receptor activity. In this invention, a conformational change in β-arrestin is monitored through a modulation of the RET signal.

The arrestins exemplified in the present invention are human β-arrestins (hβarr) and mutants and variants thereof; however, other arrestins are contemplated, including proteins having at least 60%, at least 70%, at least 80%, at least 85%, at least 90%, at least 92%, at least 94%, at least 96%, at least 98%, or at least 99% sequence identity with hβarr1, hβarr2, or with another arrestin, wherein such proteins interact with GPCRs.

Resonance Energy Transfer Assays:

Resonance energy transfer (abbreviated RET, and also referred to as Förster resonance energy transfer) is a mechanism describing energy transfer between two chromophores, having overlapping emission/absoprtion spectra. When the two chromophores (the "donor" and the "acceptor"), are within 10-100 Å (Angstroms) of one another and their transition dipoles are appropriately oriented, the donor chromophore is able to transfer its excited-state energy to the acceptor chromophore through non-radiative dipole-dipole coupling.

Bioluminescence Resonance Energy Transfer (BRET) Assay is a proximity assay based on the non-radiative transfer of energy between a donor bioluminophore (bioluminescent enzyme (ex: luciferase)) and an acceptor fluorophore (ex: GFP or YFP).

As used herein, BRET1 uses coelenterazine h as the luciferase substrate (i.e. bioluminescent initiator molecule) and YFP and its variants as the energy acceptor. BRET2 uses coelenterazine 400a (Perkin-Elmer, Wellesley, Mass., USA and, Biotium Inc, Hayward, Calif., USA) as the luciferase substrate and CFP, GFP2, GFP10, Tsapphire or mAmetrine as the energy acceptor. BRET1 and BRET2 represent different variants of BRET that are based on the use of different, luminescent enzymes, luciferase substrates and different fluorescent proteins. The difference between the BRET1 and BRET2 biosensors as used herein also incorporates differences in both the linkers used to join the chromophores to the beta arrestin molecules and the orientation of the chromophores relative to each other (i.e. to which terminal of beta-arrestin are they linked.

Each version of BRET typically uses a different coelenterazine to be able to excite the acceptor at different wavelengths. Typically, the acceptor for BRET1 is a YFP and for BRET3 is an OFP (Abhijit De, Pritha Ray, Andreas Markus Loening and Sanjiv Sam Gambhir, BRET3: a red-shifted bioluminescence resonance energy transfer (BRET)-based integrated platform for imaging protein-protein interactions from single live cells and living animals *The FASEB Journal*. 23(8): 2702-2709, incorporated by reference herein) For BRET2 the acceptor is typically any fluorophore that can be excited close to 400 nM such as BFP, Cyan, GFP or mKeima (RFP).

(i) bioluminophore: The bioluminophore in the BRET assay is a protein, that catalyzes the reaction of a substrate (i.e. a bioluminescent initiator molecule) producing bioluminescence.

Luciferase is an example of a protein that catalyzes the oxidation of its substrate (ex: coelenterazine) producing light, and can be used as a bioluminophore. As used herein, luciferases refer to an enzyme that catalyzes a bioluminescent reaction (a reaction that produces bioluminescence). In representative embodiments, the subject luciferase polypeptides are polypeptide sequences of the *Renilla reniformis* wild-type and mutant luciferases, which are known and reported in Lorenz et al., Proc. Natl. Acad. Sci. USA (1991) 88:4438-4442, Loening et al., Protein Eng Des Sel. (2006) 19(9):391-400, and also reported in U.S. Pat. No. 6,451,549 as SEQ ID NOS: 1 and 2, and in U.S. Pat. No. 7,842,469, the disclosure of which is herein incorporated by reference.

In representative embodiments, the subject luciferase polypeptides may also be mutants (also referred to as variants herein) of wild-type luciferases found in *Renilla* species (e.g., *Renilla koellikeri; Renilla muelleri* and *Renilla reniformis*, where in representative embodiments, the mutant luciferase is a mutant of the *Renilla reniformis* wild-type luciferase). The term "mutant" is employed broadly to refer to a protein that differs in some way from a reference wild-type protein, where the subject protein retains at least one biological property of the reference wild-type (e.g., naturally occurring) protein. The term "biological property" of the subject proteins includes, but is not limited to, spectral properties, such as emission maximum, quantum yield, and brightness (e.g., as compared to the wild-type protein or another reference protein such as firefly luciferase from *P. pyralis*), and the like; in vivo and/or in vitro stability (e.g., half-life); and the like. In particular, the mutants (or variants) retain luciferase activity (e.g., catalyze the conversion of a coelenterazine substrate into a luminescent product in the presence of molecular oxygen). Mutants of the disclosure include single amino acid changes (point mutations), deletions of one or more amino acids (point-deletions), N-terminal truncations, C-terminal truncations, insertions, and the like.

For purposes of the disclosure, a naturally occurring luciferase is a reference wild type luciferase for a given mutant if the amino acid sequences of the wild-type and the mutant have high identity over at least the length of the mutant (e.g., at least about 90%, at least about 95%, at least about 97%, at least about 98%, at least about 99% or higher) but will not have complete sequence identity in representative embodiments.

In representative embodiments, the mutants encoded by the subject polynucleotides exhibit increased light output as compared to their corresponding reference wild-type protein. Specifically, the subject mutants have at least enhanced light output with a given coelenterazine substrate as compared to their corresponding reference wild type. For purposes of the present disclosure, increased light output is determined by evaluating at least one of the kinetics and quantum yield of a given mutant using a convenient assay known to those of skill in the art. In representative embodiments in which the subject polynucleotides encode a mutant of Renilla luciferase that exhibits enhanced light output, the encoded mutant may include a substitution at at least one of the following positions: C124; K136; M185; and S287. In one aspect the Renilla luciferase mutant has the following substitutions: C124A and M185V. In another aspect the Renilla luciferase mutant has the following substitutions: A55T, C124A and M185V, and is referred to herein as RlucII. These mutations and variations thereof are known (see Loening et al., Protein Eng Des Sel. (2006) 19(9):391-400 and U.S. Pat. No. 7,842,469, both of which are incorporated herein), and are contemplated for use in the present invention. Examples of Renilla luciferase proteins contemplated herein include proteins that have an amino acid-sequence selected from:

```
Rluc WT
                                         (SEQ ID NO: 2)
MTSKVYDPEQRKRMITGPQWWARCKQMNVLDSFINYYDSEKHAENAVIF

LHGNAASSYLWRHVVPHIEPVARCIIPDLIGMGKSGKSGNGSYRLLDHY

KYLTAWFELLNLPKKIIFVGHDWGACLAFHYSYEHQDKIKAIVHAESVV

DVIESWDEWPDIEEDIALIKSEEGEKMVLENNFFVETMLPSKIMRKLEP

EEFAAYLEPFKEKGEVRRPTLSWPREIPLVKGGKPDVVQIVRNYNAYLR

ASDDLPKMFIESDPGFFSNAIVEGAKKFPNTEFVKVKGLHFSQEDAPDE

MGKYIKSFVERVLKNEQ*

RlucII (A55T/C124A/M185V)
                                         (SEQ ID NO: 3)
MTSKVYDPEQRKRMITGPQWWARCKQMNVLDSFINYYDSEKHAENAVIF

LHGNATSSYLWRHVVPHIEPVARCIIPDLIGMGKSGKSGNGSYRLLDHY

KYLTAWFELLNLPKKIIFVGHDWGAALAFHYSYEHQDKIKAIVHAESVV

DVIESWDEWPDIEEDIALIKSEEGEKMVLENNFFVETVLPSKIMRKLEP

EEFAAYLEPFKEKGEVRRPTLSWPREIPLVKGGKPDVVQIVRNYNAYLR

ASDDLPKMFIESDPGFFSNAIVEGAKKFPNTEFVKVKGLHFSQEDAPDE

MGKYIKSFVERVLKNEQ*

Rluc8 (A55T/C124A/S130A/K136R/A143M/M185V/M253L/
S287L)
                                         (SEQ ID NO: 4)
MASKVYDPEQRKRMITGPQWWARCKQMNVLDSFINYYDSEKHAENAVIF

LHGNATSSYLWRHVVPHIEPVARCIIPDLIGMGKSGKSGNGSYRLLDHY

KYLTAWFELLNLPKKIIFVGHDWGAALAFHYAYEHQDRIKAIVHMESVV

DVIESWDEWPDIEEDIALIKSEEGEKMVLENNFFVETVLPSKIMRKLEP

EEFAAYLEPFKEKGEVRRPTLSWPREIPLVKGGKPDVVQIVRNYNAYLR

ASDDLPKLFIESDPGFFSNAIVEGAKKFPNTEFVKVKGLHFLQEDAPDE

MGKYIKSFVERVLKNEQ
``` portions thereof, mutants thereof, variants thereof, or conservative variants thereof. Other luciferase variants known in the art include those disclosed in US 2009/0136998, incorporated by reference herein.

In representative embodiments, the mutant luciferase polynucleotides encoded by the nucleic acids are mutants of luciferase polynucleotides that employ a coelenterazine as a substrate, where the term coelenterazine refers collectively to native coelenterazine, as well as analogues thereof, where representative coelenterazine analogues of interest include, but are not limited to: benzyl-coelenterazine; coelenterazine-cp; coelenterazine-n; bis-deoxy-coelenterazine (also known as coelenterazine 400a and DeepBlue-coelenterazine); and the like.

In addition to the above-described specific subject polynucleotide compositions, also of interest are homologues of the above-sequences. With respect to homologues of the subject polynucleotide, the source of homologous genes may be any species of plant or animal, or the sequence may be wholly or partially synthetic. In certain embodiments, sequence similarity between homologues is at least about 20%, at least about 25%, and may be 30%, 35%, 40%, 50%, 60%, 70% or higher, including 75%, 80%, 85%, 90% and 95% or higher. Sequence similarity is calculated based on a reference sequence, which may be a subset of a larger sequence, such as a conserved motif, coding region, flanking region, and the like. A reference sequence will usually be at least about 18 nt long, more usually at least about 30 nt long, and may extend to the complete sequence that is being compared. Algorithms for sequence analysis are known in the art, such as BLAST, described in Altschul et al. (1990), J. Mol. Biol. 215:403-10 (using default settings, e.g. parameters w=4 and T=17). The sequences provided herein are used for recognizing related and homologous nucleic acids in database searches.

(ii) fluorophore: The fluorophore in the BRET assay is a fluorescent protein.

Green fluorescent protein ("GFP") is a 238 amino acid residues polypeptide with amino acid residues 65 to 67 involved in the formation of the chromophore, which does not require additional substrates or cofactors to fluoresce (see, e.g, Prasher et al, 1992, Gene 111:229-233; Yang et al, 1996, Nature Biotechnol. 14:1252-1256; and Cody et al, 1993, Biochemistry 32:1212-1218). Thus, in one embodiment, such a fluorophore is a green fluorescent protein (GFP) (referring to native Aequorea green fluorescent protein), and variants thereof.

A broad range of fluorescent protein genetic variants have been developed over the past several years that feature fluorescence emission spectral profiles spanning almost the entire visible light spectrum. Such variants of the GFP gene have been found useful to enhance expression and to modify excitation and fluorescence. Extensive mutagenesis efforts in the original jellyfish protein have resulted in fluorescent probes that range in color from blue to yellow. For example, substitution of a serine at position 65 to either alanine, glycine, isoleucine, or threonine results in mutant GFPs with a shift in excitation maxima and greater fluorescence than wild type protein when excited at 488 nm (see, e.g, Heim et al, 1995, Nature 373:663-664; U.S. Pat. No. 5,625,048; Delagrave et al, 1995, Biotechnology 13:151-154; Cormacketal, 1996, Gene 173:33-38; and Cramer et al, 1996, Nature Biotechnol. 14:315-319). Longer wavelength fluorescent proteins, emitting in the orange and red spectral regions, have been developed from the marine anemone *Discosoma striata* and reef corals belonging to the class Anthozoa. Still other species produce similar proteins having cyan, green, yellow, orange, red, and far-red fluorescence emission. Thus, in another embodiment, GFPs are isolated from organisms other than the jellyfish, such as, but not limited to, the sea pansy, *Renilla reriformis*, or are variants thereof.

Thus, a fluorophore, as used herein, includes wild type green fluorescent protein and its variants, as well as fluorescent proteins and variants from other species. Such fluorophores are many, and are known to those of skill in the art. They include, but are not limited to:

Green Fluorescent Proteins include GFP (wt), EGFP, Emerald, Superfolder GFP, Azami Green, mWasabi, TagGFP, TurboGFP, AcGFP, ZsGreen, T-Sapphire.

Blue Fluorescent Proteins include Blue Fluorescent Protein (BFP), EBFP, EBFP2, Azurite, GFP2, GFP10, and mTagBFP;

Cyan Fluorescent Proteins include Cyan Fluorescent Protein (CFP), ECFP, mECFP, Cerulean, CyPet, AmCyan1, Midori-Ishi Cyan, TagCFP, mCFPm$^m$, and mTFP1 (Teal);

Yellow Fluorescent Proteins include Yellow Fluorescent Protein (CFP), EYFP, Topaz, Venus, mCitrine, YPet, TagYFP, PhiYFP, ZsYellow1, and mBanana;

Orange Fluorescent Proteins include Orange Fluorescent Protein (OFP), Kusabira Orange, Kusabira Orange2, mOrange, mOrange2, dTomato, dTomato-Tandem, TagRFP, TagRFP-T, DsRed, DsRed2, DsRed-Express (T1), DsRed-Monomer, and mTangerine; and Red Fluorescent Proteins include Red Fluorescent Protein (RFP), mRuby, mApple, mStrawberry, AsRed2, mRFP1, JRed, mCherry, HcRed1, mRaspberry, dKeima-Tandem, HcRed-Tandem, mPlum, tdTomato, and AQ143.

Both green and yellow fluorescent proteins have been genetically engineered to create circular permutations of the original sequences that enable fusions to amino acids far removed from the normal amino and carboxy termini (abbreviated cpGFP and cpYFP).

The choice of a suitable fluorophore for use in a BRET assay will be known to one of skill in the art. In one embodiment, fluorophores include green fluorescent protein—wild type (GFP-wt), yellow fluorescent protein (YFP), Venus, Topaz, ZsYellow1, mOrange2, mKeima, blue fluorescent protein (BFP), cyan fluorescent protein (CFP), Tsapphire, mAmetrine, green fluorescent protein-2 (GFP2) and green fluorescent protein-10 (GFP10), or variants thereof. Fluorescent proteins having an excitation peak close to 400 nm may be particularly suitable. More particular examples of fluorophores include mAmetrine, cyan fluorescent protein (CFP), and GFP10.

Fluorescence Resonance Energy Transfer (FRET) Assay. Similar to BRET, FRET involves the transfer of energy from an excited donor fluorophore to an adjacent acceptor fluorophore. For example, CFP and YFP, two color variants of GFP, can be used as donor and acceptor, respectively.

(i) fluorophore: The fluorophores in the FRET assay are fluorescent proteins, having the same properties as the fluorophore as defined above for the BRET assay.

Two fluorophores are employed in FRET, one as donor and one as acceptor. The term "donor fluorophore-acceptor pair," as used herein, means a donor fluorophore and an acceptor that has an absorbance spectrum overlapping the emission spectrum of the donor fluorophore. Where the first member of the pair is a donor fluorophore, the second member of the pair will be an acceptor. Where the first member of the pair is an acceptor, the second member of the pair will be a donor fluorophore.

Any of a number of fluorophore combinations can be selected for use in the FRET embodiment of the present invention (see for example, Pesce et al., eds, Fluorescence Spectroscopy, Marcel Dekker, New York, 1971; White et al., Fluorescence Analysis: A practical Approach, Marcel Dekker, New York, 1970; Handbook of Fluorescent Probes and Research Chemicals, 6th Ed, Molecular Probes, Inc., Eugene, Oreg., 1996; which are incorporated herein by reference). In general, a preferred donor fluorophore is selected that has a substantial spectrum of the acceptor fluorophore. Furthermore, it may also be desirable in certain applications that the donor have an excitation maximum near a laser frequency such as Helium-Cadmium 442 nM, Argon 488 nM, Nd:YAG 532 nm, He—Ne 633 nm, etc. In such applications the use of intense laser light can serve as an effective means to excite the donor fluorophore. In certain preferred embodiments, the acceptor fluorophore has a substantial overlap of its excitation spectrum with the emission spectrum of the donor fluorophore. In some cases, the wavelength maximum of the emission spectrum of the acceptor moiety is preferably at least 10 nm greater than the wavelength maximum of the excitation spectrum of the donor moiety. Additional examples of useful FRET labels include, e.g., those described in U.S. Pat. Nos. 5,654,419, 5,688,648, 5,853,992, 5,863,727, 5,945,526, 6,008,373, 6,150,107, 6,177,249, 6,335,440, 6,348,596, 6,479,303, 6,545,164, 6,849,745, 6,696,255, and 6,908,769 and Published U.S. Patent Application Nos. 2002/0168641, 2003/0143594, and 2004/0076979, the disclosures of which are incorporated herein by reference.

As indicated above, the donor and acceptor fluorophores should be capable of forming a FRET pair. Many suitable fluorophore pairs are familiar to those of skilled in the art. In one embodiment, the FRET pair comprises one of CFP-YFP, GFP-mRFP1, YFP-mRFP1, GFP-RFP, sCFP3A-sYFP2, as well as sCFP3A in combination with circular permutations of sYFP2 (such as cp145, cp173, and cp229).

Circular permutations can be made by PCR. Such permutations have been described (see U.S. Pat. No. 6,699,687 and Takeharu Nagai, Shuichi Yamada, Takashi Tominaga, Michinori Ichikawa and Atsushi Miyawaki (2004) PNAS101(29): 10554-10559, incorporated by reference herein). They create variants of a FRET sensor with different orientations of the donor vs acceptor's chromophore.

Linkers

The chromophores are each attached to the beta-arrestin molecule through independent linkers. Linkers may be employed to provide the desired conformation of the BRET/FRET label chromophores within the labeled compound, e.g., including the separation between chromophores in a BRET/FRET pair. The linkers may be bound to the C-terminal, the N-terminal, or at an intermediate position.

In one embodiment, the linkers are peptide linkers, typically ranging from 2 to 30 amino acids in length. The composition and length of each of the linkers may be chosen depending on various properties desired such as flexibility and aqueous solubility. For instance, the peptide linker may comprise relatively small amino acid residues, including, but not limited to, glycine; small amino acid residues may reduce the steric bulk and increase the flexibility of the peptide linker. The peptide linker may also comprise polar amino acids, including, but not limited to, serine. Polar amino acid residues may increase the aqueous solubility of the peptide linker. Furthermore, programs such as Globplot 2.3 (http://globplot.embl.de/cgiDict.py), may be used to help determine the degree of disorder and globularity, thus also their degree of flexibility.

By way of example, contemplated linkers include: GDLRRALENSHASAGYQACGTGS (SEQ ID NO:5) and CLEDPRVPVAT (SEQ ID NO:6). Short and relatively flexible linkers include GSAGT (SEQ ID NO:7) and KLPAT (SEQ ID NO:8). Longer 15-residues long linkers, such as GSAGTGSAGTGSAGT (=3×GSAGT linker; SEQ ID NO:9) and KLPATKLPATKLPAT (=3×KLPAT linker; SEQ ID NO:10) are also contemplated; these latter 2 linkers are predicted (Globplot 2.3//globplot.embl.de/cgiDict.py) to be disordered and non-globular sequences, and thus flexible. Alpha-helix structured rigid linker, REAAAREAAAREAAAR (16-residues long; SEQ ID NO:11), is also contemplated.

The linkers may be attached to the beta-arrestin at the N-terminus, the C-terminus, or between the two termini of the beta-arrestin. When attaching in between the two termini, the linker may be attached, for instance to the first or second loop of the beta-arrestin.

Methods

Expression vectors. Plasmids encoding Flag-AT1aR, CCR5 (Pleskoff et al, 1997) and Myc-PAFR (Marrache et al, 2002) were provided by S. Meloche, N. Heveker and S. Chemtob, respectively (Université de Montréal, Québec, Canada) and WT β-arr2 was a generous gift from S. Marullo (Institut Cochin, Paris). Myc-V2R and HA-V1 aR (Terrillon et al, 2003), Myc-β2-AR (Hebert et al, 1996), Myc-δ-OR (Petaja-Repo et al, 2002), V2R-GFP (Charest & Bouvier, 2003), β2-AR-GFP (Mercier et al, 2002).

BRET1 biosensors: β-arr2-YFP (Angers et al, 2000) and Luc-β-arr2 (Perroy et al, 2003) have been described previously. Luc-β-arr-YFP was generated by subcloning the coding sequence of enhanced YFP in-frame at the C terminus of β-arr2 in pcDNA3.1-Luc-β-arr2, yielding Luc-β-arr-YFP with flexible spacers of 23 aa between Luc and β-arr, and 10 aa between β-arr and YFP. Mutation of arginine 169 into glutamate in Luc-β-arr (R169E)-YFP was generated by PCR site-directed mutagenesis using Luc-β-arr-YFP. It should be noted that while the construct described here is specific for Luc-β-arr-YFP, a construct leading to the production of a YFP-β-arr-Luc biosensor is feasible. Moreover, the resulting biosensor, YFP-β-arr-Luc, would be expected to function in the same manner as Luc-β-arr-YFP. Similarly, DNA constructs may be devised for the specific expression of Luc-β-arr-GFP, GFP-β-arr-Luc biosensors, and variants thereof.

BRET2 biosensors: Acceptor-beta-arr1/2-RlucII, with Acceptor being either mAmetrine, sCFP3A or GFP10, were derived from previously published GFP10-EPAC-RlucII fusion protein (Leduc et al. JPET 2009) by excising the EPAC coding sequence with Acc65I-HindIII restriction enzymes and replacing it with a PCR-amplified coding sequence of human beta-arrestin1 or beta-arrestin2. Sequence integrity was confirmed by DNA sequencing.

Cell culture. Human embryonic kidney 293 (HEK293) cells and simian kidney fibroblast (COS) cells were maintained as described previously (Charest & Bouvier, 2003). Cells were transfected with the indicated plasmids using the calcium phosphate precipitation method (Sambrook et al, 1989) or the FuGENE 6 transfection reagent (Roche Applied Science, Laval, Canada) according to the manufacturer's protocol. The experiments were performed 48 h after transfection.

Fluorescence microscopy. To detect Myc-β2-AR and Myc-V2R, cells were incubated with anti-Myc 9E10 monoclonal antibody (ascite fluid from our core facility) for 1 h at 4° C. and then treated with the appropriate agonist (Sigma, Oakville, Canada) for 2 or 30 min at 37° C. Cells were then fixed and permeabilized before adding Texas-red-conjugated secondary antibody (Santa Cruz Biotechnology Inc., Santa Cruz, Calif., USA). The samples were analysed by confocal laser-scanning microscopy using a Leica TCS SP1. Measurements were as follows: YFP (green), $\lambda ex=488$ nm, $\lambda em=540/25$ nm; Texas red (red), $\lambda ex=568$ nm, $\lambda em=610/30$ nm.

BRET assays. Assessment of β-arr recruitment in BRET was performed as described previously (Charest & Bouvier, 2003). Briefly, cells were distributed in 96-well microplates (Corning, Corning, USA) and incubated with or without agonist for the indicated time at 25° C. The appropriate Luc substrate was added to a final concentration of 5 mM, either simultaneously with the agonist (time course) or following agonist treatment (single measurement or dose dependency), and readings were collected using a Multilabel Reader Mithras LB 940 (Berthold Technologies, Bad Wildbad, Germany). To detect BRET1 between Luc and YFP, coelenterazine h (Molecular Probes, Burlington, Canada) was used as substrate and light emission was detected at approximately 460-500 nm (Luc) and approximately 510-550 nm (YFP), whereas for BRET2 detection (Luc and GFP), coelenterazine 400a (Perkin-Elmer, Wellesley, Mass., USA or Biotium Inc, Hayward, Calif., USA) and filters at approximately 330-470 nm (Luc) and approximately 495-535 nm (GFP2/GFP10) were used. (Broadly speaking, ranges for the detection of light emission for BRET1 are approximately 440-510 nm (Luc) and 510-570 nm (YFP), while those for BRET2 are approximately 320-490 nm (Luc) and 490-550 nm (GFP)). The BRET signal was determined by calculating the ratio of the light emitted by the fluorescent acceptor and the light emitted by Luc. The values were corrected by subtracting the background BRET signals detected when Luc-β-arr was expressed alone. Expression levels of the different receptors transfected were verified by enzyme-linked immunosorbent assay (ELISA) (Charest & Bouvier, 2003).

Receptor endocytosis assay. Receptor endocytosis was measured by ELISA as described previously (Charest & Bouvier, 2003).

Z'-factor determination. HEK293T cells were cultured in DMEM supplemented with 10% fetal bovine serum, 100 units/ml penicillin and streptomycin (Wisent Inc). $3.0 \times 10^6$ cells were seeded in 10 cm dishes. Transient transfection was performed using polyethyleneimine (PEI; Polysciences) at a DNA:PEI ratio. 24 h post-transfection, cells were detached, seeded in pretreated poly-L-ornithine hydrobromide (Sigma-Aldrich) 96-well white plates at 50,000 cells per well, and re-incubated at 37° C. for an additional 24 h before being processed. Cells were washed once with Tyrode's buffer directly in the 96-well plates and incubated in buffer with or without 100 nM of AVP for 25 to 35 min. Coelenterazine 400A was added to a final concentration of 5 μM in Tyrode's buffer 5 min before reading. Readings were collected as a sequential integration of the signals detected in the 480±20 and 530±20 nm window for the RlucII *Renilla* luciferase and GFP10 light emissions, respectively. The BRET signal was determined by calculating the ratio of the light intensity emitted by the GFP10 over the light intensity emitted by the RLucII.

Results

Double-brilliance β-arr sensor (BRET1): Inspired by previous reports of intramolecular fluorescence resonance energy transfer (FRET)-based biosensors (Zhang et al, 2002)

showing that resonance energy transfer (RET) is sensitive to changes in the relative positions of the donor and acceptor molecules, the feasibility of monitoring whether conformational changes of β-arr using an intramolecular BRET approach was assessed. A double-brilliance β-arr was engineered in which Luc was fused to the N terminus of β-arr2 and YFP to its C terminus, yielding Luc-β-arr-YFP (FIG. 1). To test the functionality of Luc-β-arr-YFP, the ability of this molecule to be recruited to agonist-stimulated class A (receptors interacting transiently with βarr) β2-adrenergic receptor (β2-AR) and class B (receptors interacting stably with βarr) V2 vasopressin receptor (V2R) by fluorescence microscopy was determined. As shown in FIG. 2A, agonist stimulation led to rapid translocation of Luc-β-arr-YFP to the plasma membrane, colocalizing with Myc-tagged β2-AR and V2R (Myc-β2-AR; Myc-V2R). The patterns of Luc-β-arr-YFP interaction were consistent with those observed for class A (transient β-arr interaction) and B (stable β-arr association) receptors in similar experiments using a β-arr-green fluorescent protein (GFP) conjugate (Oakley et al, 2000). Indeed, whereas Luc-β-arr-YFP was recruited to both β2-AR and V2R after 2 min of stimulation, it returned to the cytoplasm after 30 min in Myc-β2-AR-expressing cells but remained colocalized with Myc-V2R in endocytic vesicles.

Figure 2B:
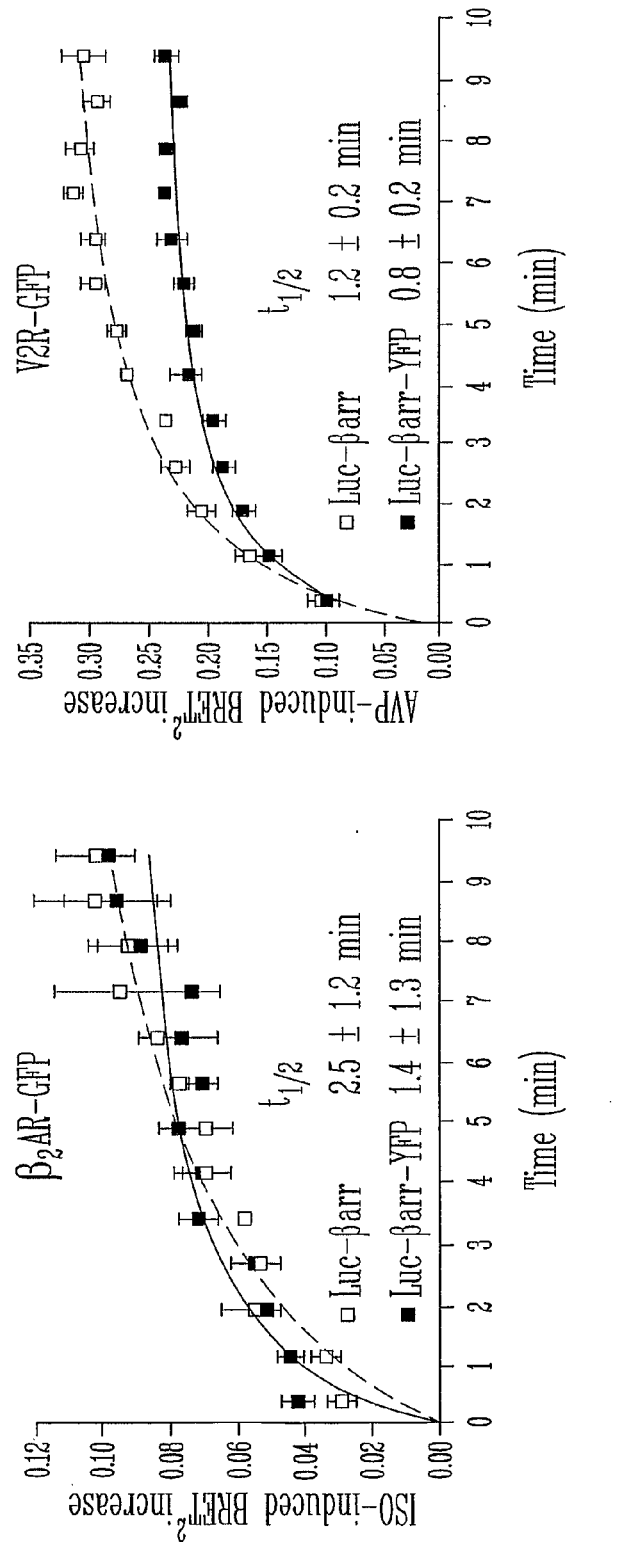
Figure 2C:
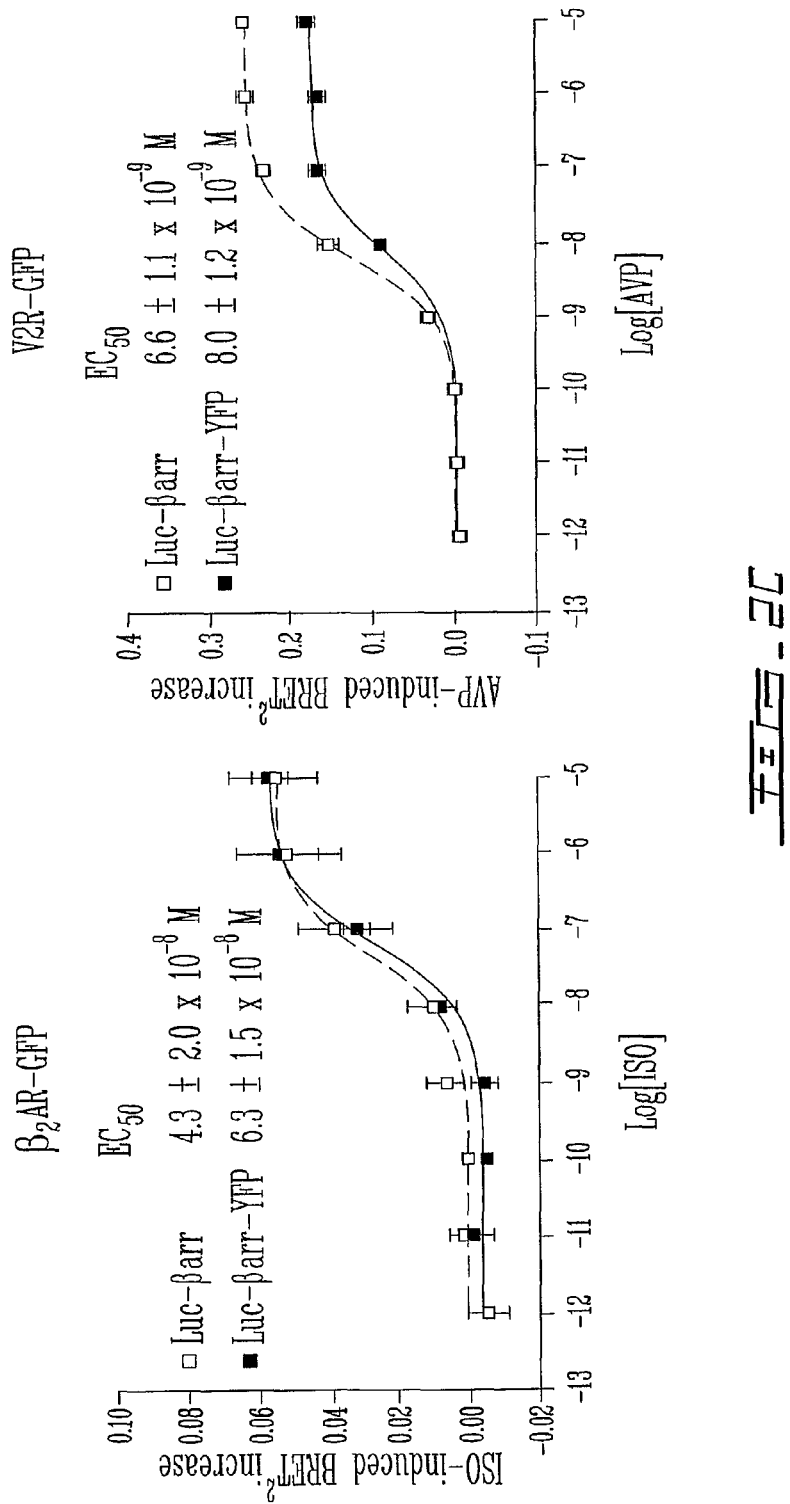
Figure 20:
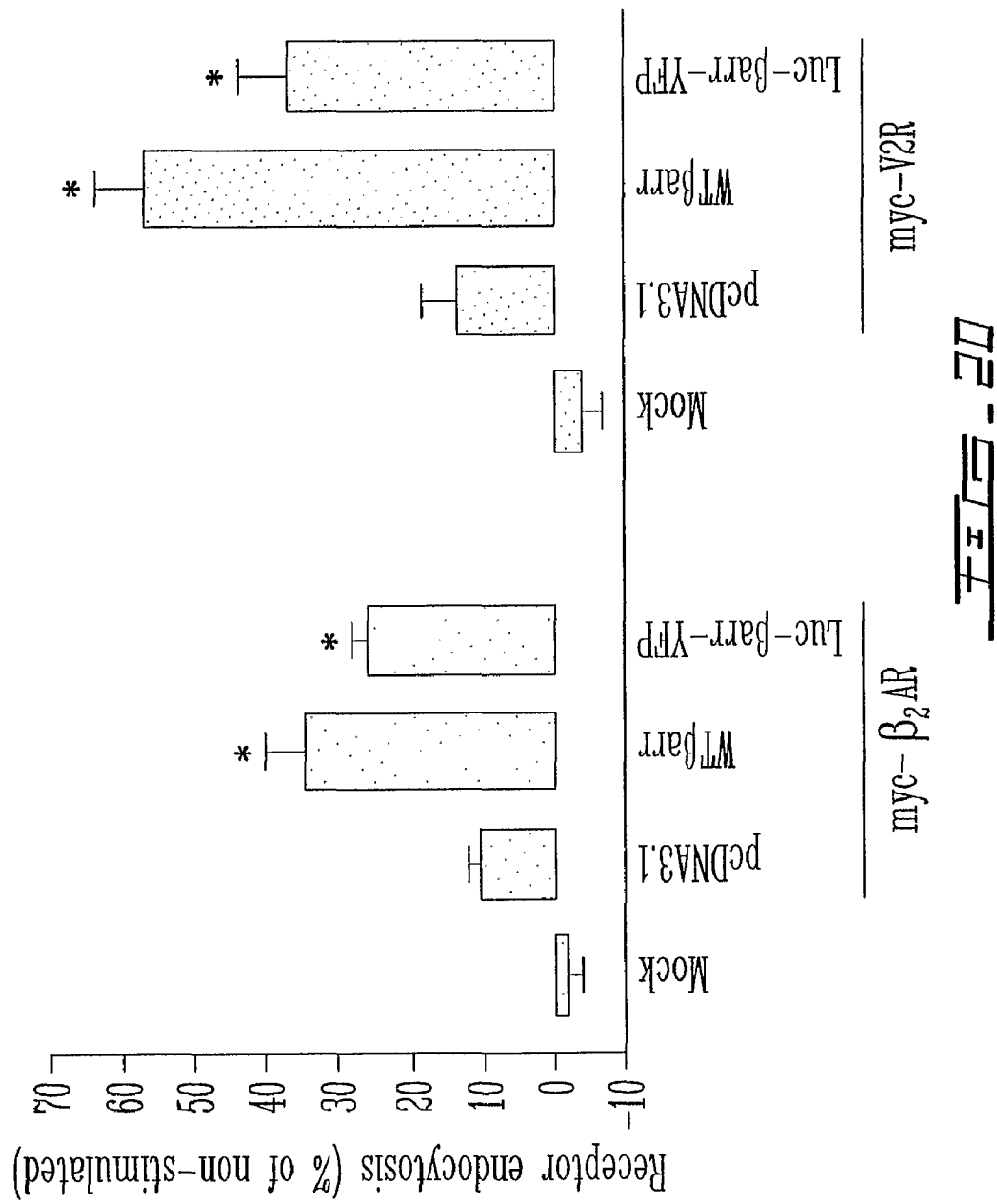

To quantitatively assess the recruitment of Luc-β-arr-YFP to agonist-activated GPCRs, an intermolecular BRET2 assay that takes advantage of the different spectral properties of Luc substrates that allow energy transfer to different fluorescent acceptors (Milligan, 2004) was used. Luc-β-arr-YFP was transiently coexpressed with the receptors, and the agonist-induced BRET2 between Luc-β-arr-YFP and either β2-AR-GFP or V2R-GFP was measured in the presence of DeepBlueC™ coelenterazine, allowing transfer of energy to GFP. As shown in FIG. 2, agonist stimulation promoted a time-dependent (FIG. 2B) and dose-dependent (FIG. 2C) increase in BRET2, reflecting the recruitment of Luc-β-arr-YFP to the receptors. Similar kinetics and EC50 were obtained for the recruitment of both Luc-β-arr-YFP and Luc-β-arr, indicating that double-brilliance β-arr is as efficiently recruited to the receptors as the singly conjugated construct. It should be noted that, although the maximum agonist-promoted BRET increase observed with the class A β2-AR is less than that observed with the class B V2R, the stability of the signals was similar, indicating that the signal observed with β2-AR reflects a steady state corresponding to constant association and dissociation of β-arr from the activated receptors.

To assess the biological activity of Luc-β-arr-YFP, its capacity to promote receptor endocytosis in COS cells, which express low endogenous levels of β-arr, was tested. As shown in FIG. 2D, agonist-promoted β2-AR and V2R endocytosis was considerably increased when overexpressing Luc-β-arr-YFP. Even though this increase in receptor endocytosis was not as pronounced as that obtained by the overexpression of wild-type (WT) β-arr, it suggests that Luc-β-arr-YFP retains significant biological activity.

Figure 3A:
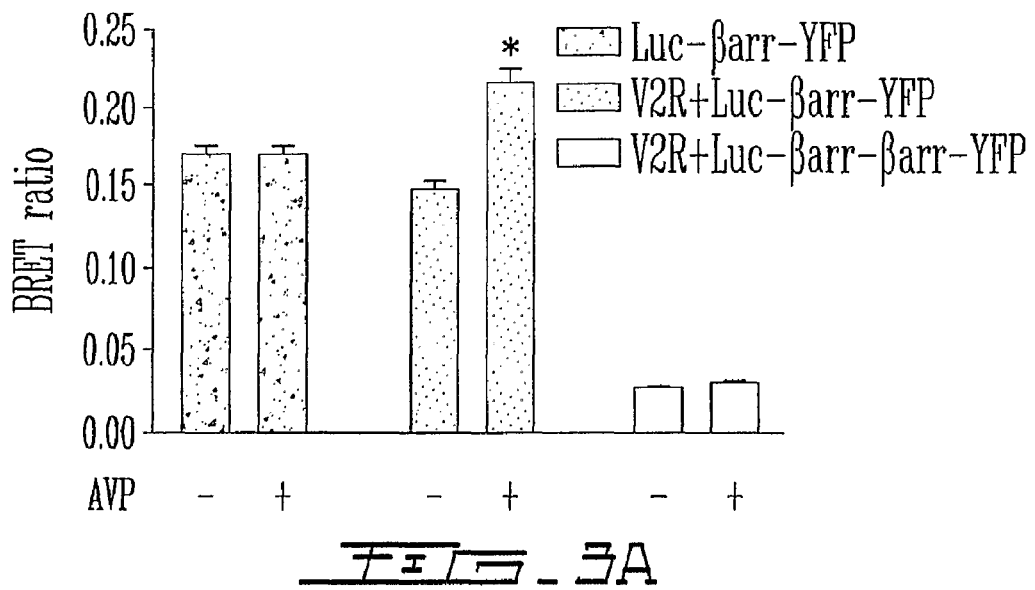
FIG. 3: AVP-induced conformational change of β-arr monitored by intramolecular BRET1. HEK293 cells were transfected with the indicated plasmids and BRET was measured at 25° C. in the presence of coelenterazine h. (A) Specificity of agonist-induced β-arr intramolecular BRET1. (B) Real-time BRET measurements of the agonist-induced β-arr conformational change. t½=half-time of maximal conformational change of β-arr. (C) Dose-dependent agonist-promoted increase of β-arr intramolecular BRET1. Cells were stimulated with increasing concentrations of AVP for 4 min. EC50=concentration of AVP producing half-maximal conformational change of β-arr. Data are the mean±s.e.m. of at least three independent experiments. *P<0.01 between treated and control condition.

Agonist-induced conformational changes of β-arr: To assess whether Luc-β-arr-YFP could be used to monitor the conformational rearrangement of β-arr upon receptor activation, the construct was expressed with and without V2R, and BRET was measured in the presence of coelenterazine h, allowing transfer of energy to YFP. As shown in FIG. 3A, an important basal BRET signal could be measured in cells transfected with Luc-β-arr-YFP, reflecting the proximity of the energy donor and acceptor in the construct. Arginine vasopressin (AVP) stimulation of cells coexpressing V2R led to a significant increase in BRET, suggesting movement of Luc and YFP relative to each other. To rule out the possibility that this increased signal results from intermolecular BRET between individual Luc-β-arr-YFP molecules brought together through oligomerization (Hirsch et al, 1999) or clustering at the plasma membrane, the occurrence of BRET in cells transiently expressing Luc-β-arr and β-arr-YFP was determined. In transfection conditions leading to equivalent fluorescence and luminescence levels as those obtained in Luc-β-arr-YFP-expressing cells, coexpression of Luc-β-arr and β-arr-YFP led to the detection of only a marginal basal BRET that could not be modulated by V2R stimulation (FIG. 3A). This observation demonstrates that the AVP-induced increase in BRET signal observed in cells transfected with Luc-β-arr-YFP results from a change in intramolecular BRET. As variations in RET can reflect changes in both the distance and orientation between the energy donor and acceptor molecules (Andrews & Demidov, 1999), the observed agonist-promoted increase in the Luc-β-arr-YFP intramolecular BRET could indicate that the N terminus and C terminus are either brought closer or are in a more permissive BRET orientation following activation.

Figure 3B:
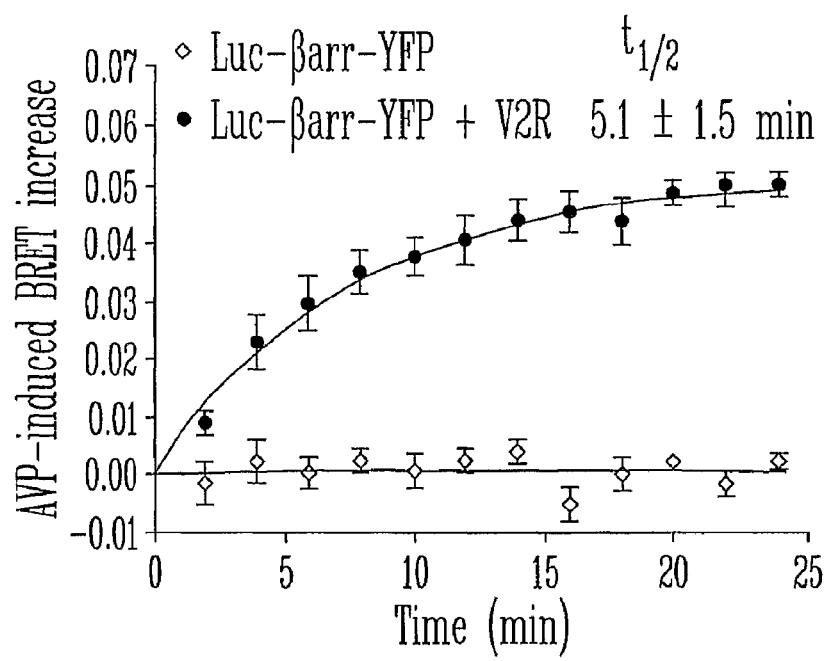
Figure 3C:
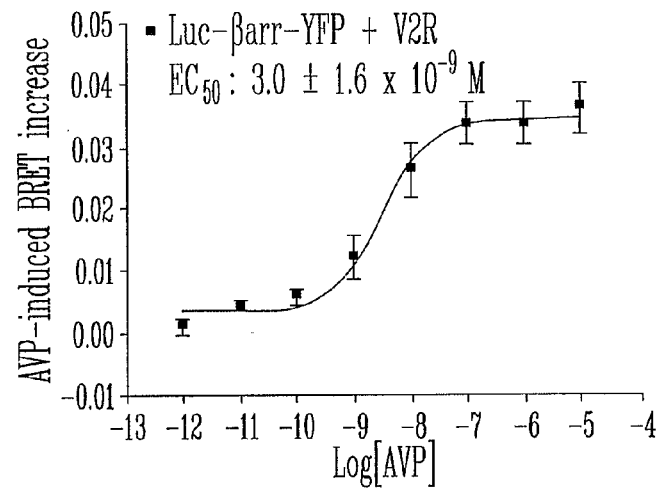

To further characterize the agonist-induced change in the conformation of β-arr, the kinetics and dose dependency of AVP-mediated BRET increase were assessed. Real-time BRET measurements show a time-dependent AVP-induced conformational change of β-arr, with half-time of maximal BRET increase (t½) of 5.1±1.5 min (FIG. 3B). The kinetics are significantly slower (P<0.02) than that of the AVP-induced recruitment of β-arr (t½=0.8±0.2 min; FIG. 2B, right panel), suggesting that the conformational change observed in Luc-β-arr-YFP occurs after its initial recruitment to the activated V2R. The difference in kinetics cannot result from inter-experimental variations because similar results were obtained when the two events were measured in the same cell population expressing V2R-GFP and Luc-β-arr-YFP (data not shown). Despite the difference in kinetics, the efficacy of AVP to induce a conformational change in Luc-β-arr-YFP (FIG. 3C) was similar to that observed for β-arr recruitment (FIG. 2C, right panel), indicating that these two events are directly linked and reflect the binding affinity of V2R for AVP (KD ~1×10−9 M).

Figure 4:
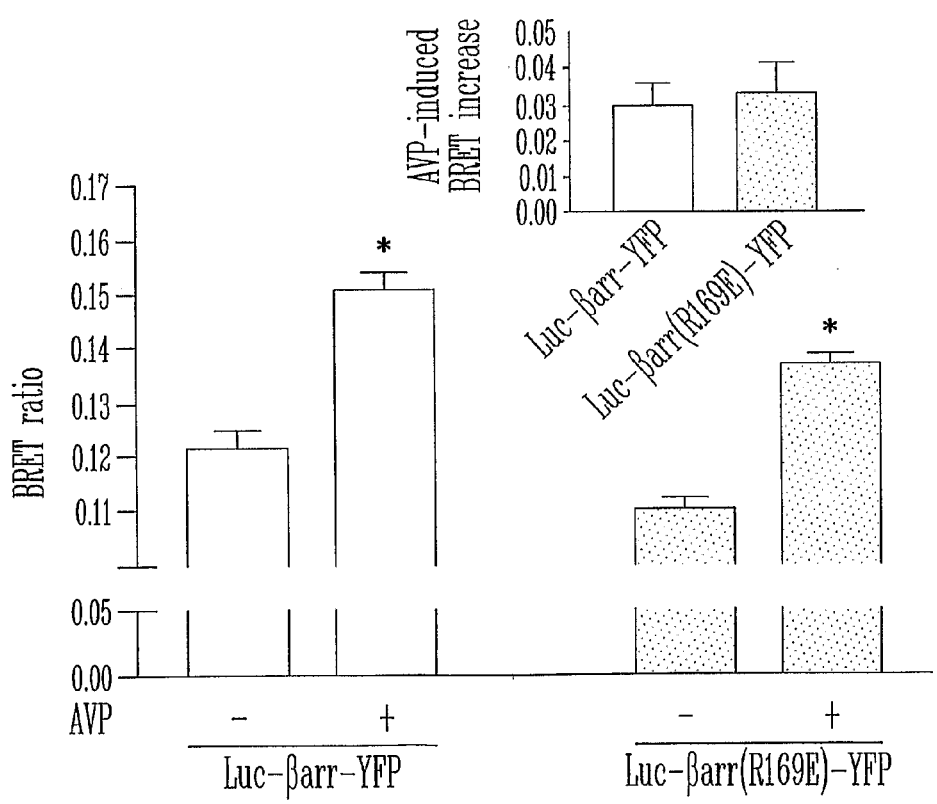
FIG. 4: Agonist-promoted conformational change of a phosphate insensitive βarrestin mutant. HEK293 cells were transfected with V2R and either Luc-βarr-YFP or Luc-βarr (R169E)-YFP. Cells were stimulated or not for 10 min with 1 μM AVP prior the addition of 5 μM coelenterazine h (Molecular Probe) and performing the intramolecular BRET1 measurements using a Multilabel Reader Mithras LB 940 (Berthold Technologies). The BRET signal was determined by calculating the ratio of the light emitted by YFP over the light emitted by Luc following the addition of coelenterazine h. The values were corrected by subtracting the background BRET signals detected when Luc-βarr was expressed alone. Inset, AVP-induced BRET increase. Data represent the mean±SEM of three independent experiments. * indicates p<0.02 between treatment and each individual control condition.

The observed kinetic lag between β-arr recruitment and its conformational change could be consistent with the proposal that inactive β-arr is first recruited to the activated GPCR where its interaction with the GRK-phosphorylated residues subsequently induces the release of its C-tail (Gurevich & Gurevich, 2003). Alternatively, such a lag could indicate that the intramolecular BRET changes observed with Luc-β-arr-YFP result from the subsequent recruitment of β-arr-interacting proteins (e.g. clathrin and AP2 or signalling proteins such as c-Src, Raf1, ERK1/2, ASK1 and JNK3) to the receptor-bound β-arr (Lefkowitz & Whalen, 2004). Interestingly, a β-arr (R169E) mutant shown to bind to GPCRs in a phosphorylation-independent manner, probably as a result of a constitutively open conformation (Kovoor et al, 1999) resulted, when inserted between Luc and YFP (Luc-β-arr(R169E)-YFP), in basal and AVP-stimulated BRET signals similar to those observed with WT Luc-β-arr-YFP (FIG. 4). This indicates that the engagement of βarr by the activated receptor can be detected by the double brilliance βarr independently of the phosphorylation state of the receptor.

Figure 5A:
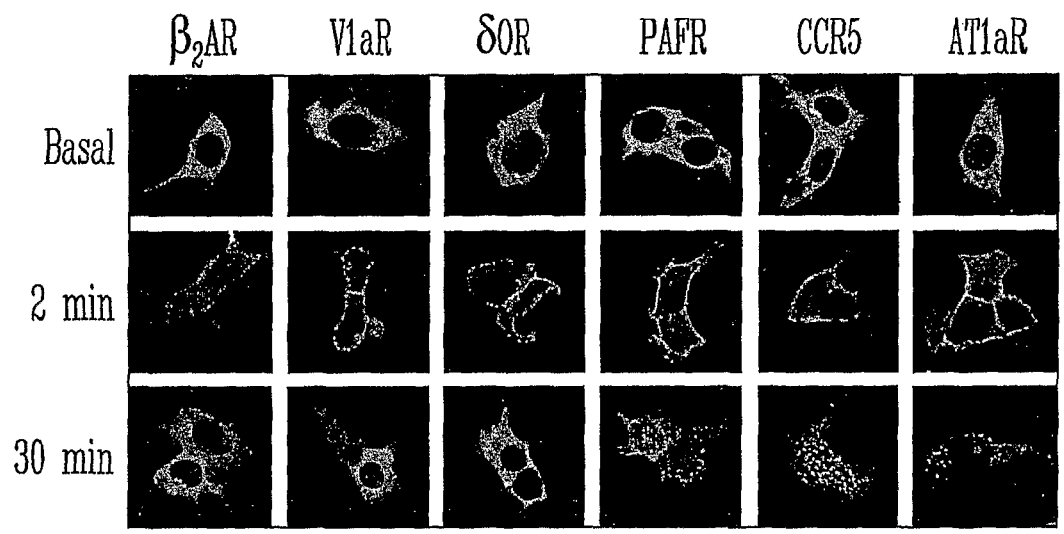
FIG. 5: Double-brilliance β-arr monitors the activation of many GPCRs. HEK293 cells were transfected with Luc-β-arr-YFP and either pcDNA3.1 or plasmids encoding the indicated receptors. (A) Agonist-induced translocation of Luc-β-arr-YFP measured following treatment with 1 mM of the specific agonists (β2-AR, ISO; V1 aR, AVP; δ-OR, SNC80; PAFR, PAF; CCR5, hRANTES; AT1aR, angiotensin II). (B) Agonist-induced conformational change of Luc-β-arr-YFP measured following 10 min stimulation with the specific agonists mentioned in (A). BRET1 was measured using a Multilabel Reader Mithras LB 940 (Berthold Technologies). The BRET signal was determined by calculating the ratio of the light emitted by YFP over the light emitted by Luc following the addition of coelenterazine h. Data are the mean±s.e.m. of three independent experiments. *P<0.05 between treatment and each individual control condition.
Figure 5B:
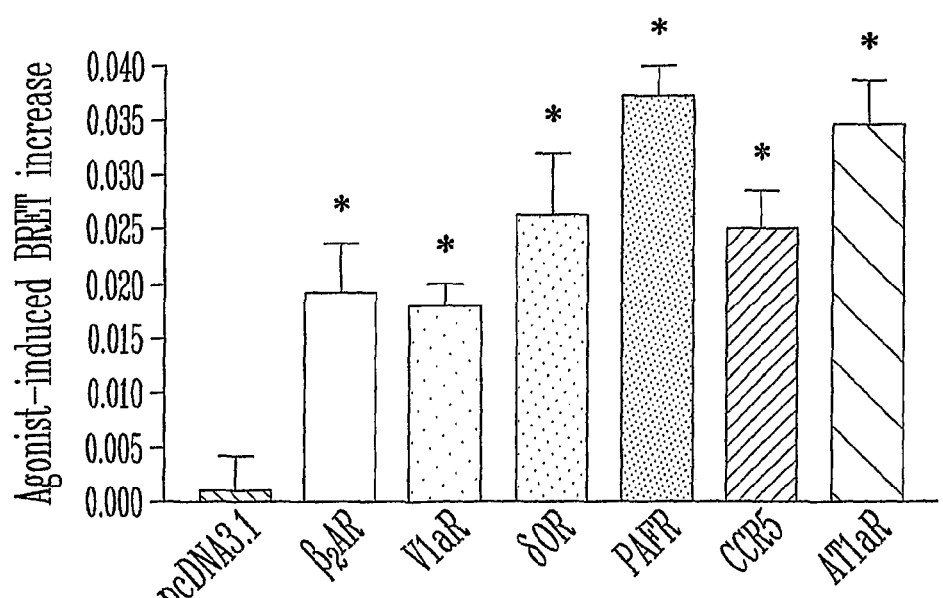

A general biosensor to monitor GPCR activity: To assess whether Luc-β-arr-YFP could be used as a general GPCR activity sensor, a determination of whether its agonist-induced conformational change could be promoted by other receptors was made, particularly those of class A, which are believed to interact only transiently with β-arr. Recruitment of Luc-β-arr-YFP and agonist promoted intramolecular BRET were assessed in cells coexpressing different receptors of class A (β2-AR, V1 vasopressin receptor (V1 aR), d-opioid receptor (δ-OR)) and class B (platelet-activating factor receptor (PAFR), CC chemokine receptor type 5 (CCR5), angiotensin receptor type 1a (AT1aR)). As shown in FIG. 5A, agonist stimulation efficiently induced the recruitment of Luc-β-arr-YFP to the plasma membrane, with the expected interaction patterns for all class A (transient) and class B (stable) receptors. In all cases, activation of Luc-β-arr-YFP mediated by class A and B receptors was accompanied by a significant increase in BRET (FIG. 5B). Interestingly, although the kinetics and stability of the BRET increase were found to be similar for receptors of class A and B (data not shown), a tendency of class A receptors to induce smaller BRET increases was observed. As previously noted when comparing the BRET-detected recruitment of β-arr to class A β2-AR and class B V2R (FIG. 2B), this probably indicates that the BRET assays provide a steady-state signal reflecting continuous rounds of association-dissociation cycles. In any case, these results suggest that Luc-β-arr-YFP can be used as a general biosensor to monitor GPCR activity and that the interaction can be monitored for extended periods of time making it compatible with its use in high through put screening assays that request long lived signals. When compared with the intermolecular BRET-based β-arr recruitment assays (Angers et al, 2000; Bertrand et al, 2002), double-brilliance β-arr avoids the difficulty of expressing the appropriate ratio of energy donor and acceptor constructs and allows the study of unmodified GPCRs.

The interaction of β-arr with the GRK-phosphorylated GPCRs is thought to induce the release of β-arr's C-tail and the opening of its structure (Gurevich and Gurevich 2003), subsequently leading to the recruitment of βarrestin-interacting proteins (Lefkowitz and Whalen 2004). To assess if the conformational change of β-arr detected with the double brilliance β-arr could also be detected using βarr mutants believed to be constitutively in the open state, assessment was made of the agonist-promoted BRET signal of two other β-arr mutants (β-arr(3A): I387A, V388A, F389A; β-arr(IV): I387A, V388A),inserted between Luc and YFP (Luc-βarr (3A)-YFP and Luc-βarr(IV)-YFP). These mutant β-arrs are believed to be constitutively active due to the disruption of the polar core keeping βarrestin in a closed and inactive conformation (Gurevich 1998). As shown in FIG. 6, while the basal BRET signal observed with each Luc-βarr-YFP constitutively active mutant (Luc-βarr(3A)-YFP and Luc-βarr(IV)-YFP) was found to be similar to that of wild-type Luc-βarr-YFP, the agonist-induced BRET increase was significantly reduced by the mutations (FIG. 6, inset).

In addition to agonists, the activity of ligands with inverse agonist efficacy towards specific signalling pathways can be detected by the double brilliance β-arr. As shown in FIG. 7, the V2R inverse agonist SR121463 that inhibits cyclic AMP production can promote an increase in the BRET signal in cells co-expressing wild type V2R and Luc-β-arr-YFP.

Double brilliance β-arr may also prove to be an effective tool in the study of the increasingly diverse roles played by β-arr, such as its involvement with receptors other than GPCRs and diverse signaling molecules in different systems (FIG. 8). A list of some of the proteins that have been shown to interact with βarr and which activity could be monitored by double brilliance β-arr is presented in Table 1. The spectrum of receptors capable of utilizing β-arr for endocytosis via clathrin binding sites has significantly increased (Lefkowitz and Whalen 2004). For example, β-arr appears to be required for engulfing Frizzled-4, an atypical seven-transmembrane domain receptor, through interaction with the adaptor protein Dishevelled-2 phosphorylated by PKC (Chen et al. 2003a); for the endocytosis of receptors with serine/threonine kinase activity such as the transforming growth factor β receptor (TGF-βR), in a manner dependent on the phosphorylation of RIII by RII (Chen et al. 2003b); as well as for the endocytosis of the IGF1 receptor, in a manner that is independent from its phosphorylation (Dalle et al. 2001). This indicates that the βarr double brillance could be a general biosensor of the activity of many distinct receptors and signalling molecules.

TABLE 1

List of proteins capable of interacting with β-arrestin

| Binding Protein | β-arrestin isoform | Type of protein |
|---|---|---|
| Clathrin | β-arr 1, 2 | trafficking |
| AP2 | β-arr 1, 2 | trafficking |
| NSF | β-arr 1 | trafficking |
| ARF6 | β-arr 2, 1 | Small G/GEFs |
| ARNO | β-arr 2 | Small G/GEFs |
| Ral-GDS | β-arr 1, 2 | Small G/GEFs |
| RhoA | β-arr 1 | Small G/GEFs |
| MAPK cascade components: | | Signaling |
| ASK1 | β-arr 1, 2 | |
| c-Raf-1 | β-arr 1, 2 | |
| JNK3 | β-arr 2, 1 | |
| ERK2 | β-arr 1, 2 | |
| Nonreceptor tyrosine kinases: | | signaling |
| c-Src | β-arr 1, 2 | |
| Yes | β-arr 1 | |
| Hck | β-arr 1 | |
| Fgr | β-arr 1 | |
| Others: | | signaling |
| Mdm2 | β-arr 1, 2 | |
| IκBα | β-arr 1, 2 | |
| PDE4D family | β-arr 1, 2 | |
| Dishevelled | β-arr 1, 2 | |
| PP2A | β-arr 1 | |

(Lefkowitz & Shenoy, 2005)

Figure 9A:
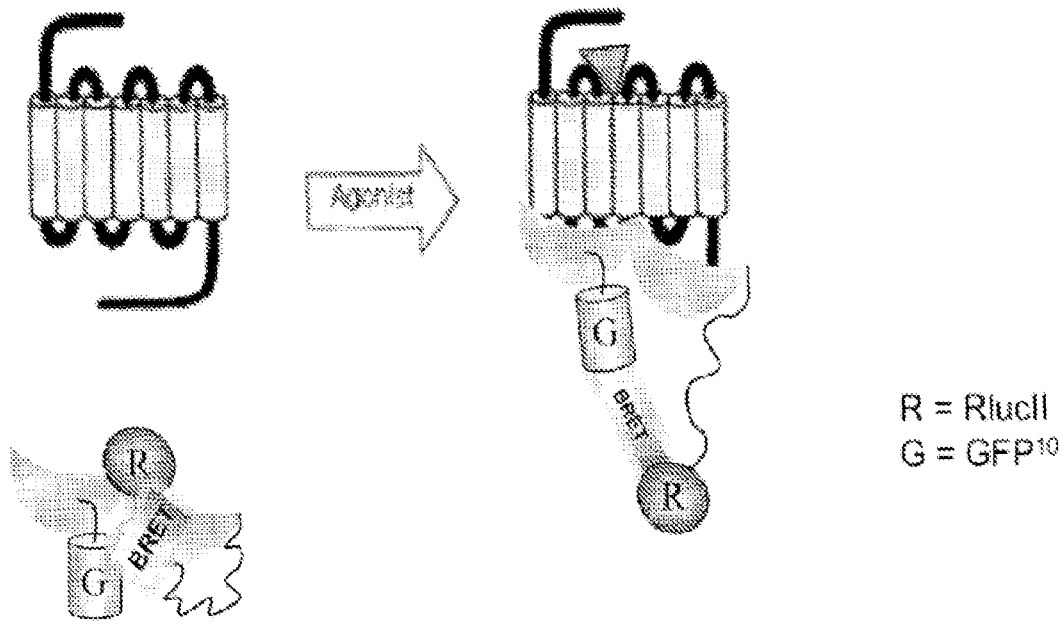
FIG. 9: Characterization of BRET2-βArrestin double-brilliance sensors. (A) Structure and activation: BRET1 and BRET2-βArrestin double brilliance (db) sensors are unimolecular with BRET tags in N- and C-terminus of a central βArrestin core. The linkers separating the BRET1 and BRET2 tags from βArrestin differ in both length and composition. For the BRET1 sensor the structure is: BRET donor (Rluc)-Linker1 (SEQ ID NO:5)-βArrestin-Linker2 (SEQ ID NO:6)-BRET1 acceptor (YFP) and for the BRET2 sensors: Structure: BRET2 acceptor (sCFP3A, mAmetrine or GFP10)-Linker3 (SEQ ID NO:7)-βArrestin-Linker4 (SEQ ID NO:8)-BRET2 donor (RlucII). For BRET1, the Rluc substrate is coelenterazine H, whereas for BRET2, the Rluc substrate is deep-blue coelentrazine. All versions of the βArrestin1 and 2 db are conformational sensors. However, following GPCR activation by an agonist (illustrated as a triangle), changes in βArrestin conformation lead to a decreased BRET signal for the BRET2 sensors while it leads to an increased BRET signal with the BRET1 sensor configuration (see FIGS. 1-7). (B) Kinetics and dose-responses measured in BRET2 with the BRET2-βARR1 and 2 db sensors, in response to V2R activation by its agonist AVP: at 100 nM for the kinetics or at increasing concentrations of AVP for dose-response experiments. (C) βARR db sensor to characterize ligands of different efficacies. Hek293 cells transiently expressing both AT1aR and GFP10-parr1-RlucII db sensor, were stimulated with a full (AngII) or partial agonists and responses were evaluated as a BRET2 signal modulation. a) Dose-dependent ligand-promoted decrease of βarrestin intramolecular BRET2 signal after a 25 min stimulation. Data are the mean+/−S.E.M. of 3 independent experiments. b) Agonist-promoted BRET changes. Cells were treated for 25 min with 1 µM AngII or 10 pM of the partial agonists. Data represent mean+/−S.E.M. of 4 independent experiments. One-way ANOVA followed by Tukey's multiple comparison post-hoc test (AngII as reference) was used to assess statistical significance. *, $p<0.05$, ***, $p<0.001$. AngII=Angiotensin 2 octapeptide, SVdF: AngII analog with $Sar_1,Val_5,D\text{-}Phe_8$ substitutions at the indicated amino acid positions in the octapeptide, SII: AngII analog with $Sar_1,Ile_4,Ile_8$ substitutions at the indicated amino acid positions in the octapeptide, SBpA: AngII analog with $Sar_1,Bpa_8$ substitutions at the indicated amino acid positions in the octapeptide, SIVI: AngII analog with $Sar_1,Ile_8$ substitutions at the indicated amino acid positions in the octapeptide, DVG: AngII analog with $Asp_1,Val_5,Gly_8$ substitutions at the indicated amino acid positions in the octapeptide.

Double-brilliance β-arr sensor (BRET2): In addition to the constructs described above, the following BRET2-based beta-arrestin 1 and 2 sensors: Acceptor (mAmetrine; sCFP3A; GFP10)-GSAGT-βArrestin1/2-KLPAT-RlucII were also made (FIG. 9a), using similar techniques, namely:
  Ametrine-hβarr1r-RlucII,
  Ametrine-hβarr2-RlucII,
  CFP-hβarr1-RlucII,
  CFP-hβarr2-RlucII,
  GFP$^{10}$-hβarr1-RlucII, and
  GFP$^{10}$-hβarr2-RlucII.

Figure 9B:
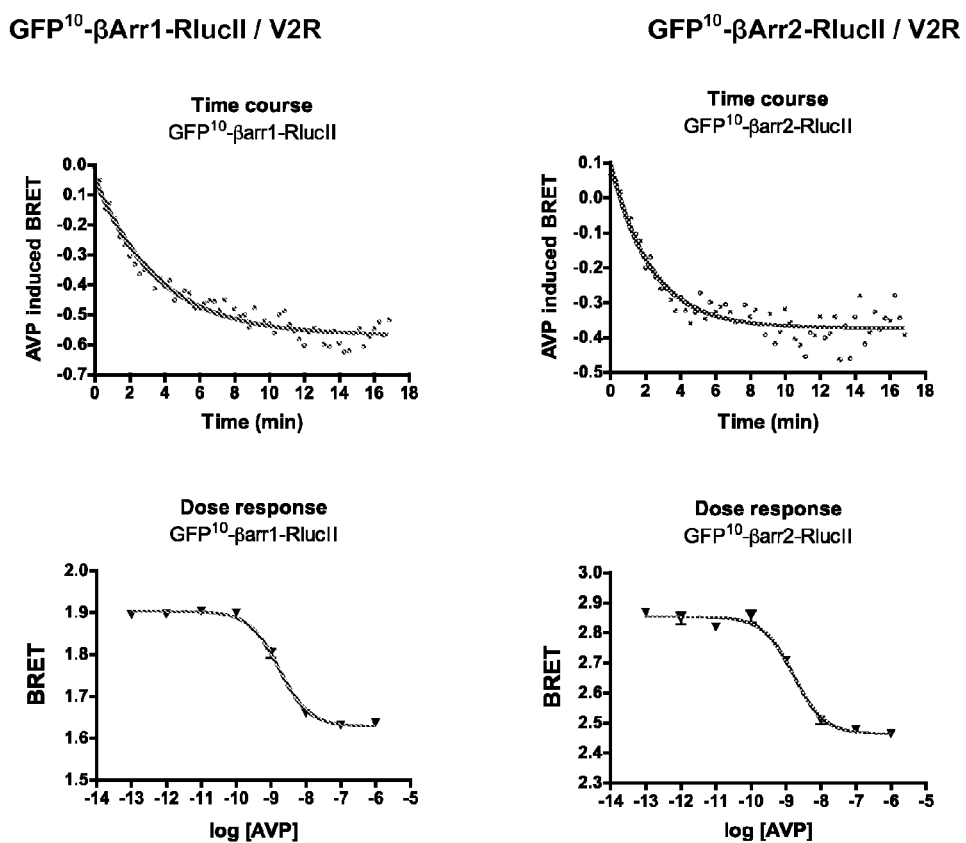

An enhanced Rluc variant (Rluc II) was used with the BRET2 versions as it provides a sustained and a stronger signal with coelenterazine 400a (200-400 times) than with the WT Rluc. The orientation of the BRET tags and nature of the linkers in these constructs differ from the BRET1 version. In contrast to the BRET1 sensors, these structure leads to a decrease BRET signal in response to an agonist-promoted GPCR activation. As shown in FIGS. 9B and 2B, this inversion of the BRET signal between the BRET1 and BRET2 versions of the beta-arrestin db sensors still lead to similar kinetics and dose-responses to an AVP stimulation of V2R. Both beta-arrestin1 and 2 sensors are functional and give similar responses for the same receptor activation (FIG. 9B).

The Z'-factor is a reflection of the robustness of an assay and should vary depending on the experimental conditions and receptor used. With cells transiently expressing both V2R and sensors a Z'-factor between 0.43 and 0.63 (FIG. 10) was obtained for both BRET1 and BRET2 versions of the beta-arrestin db sensors, providing a robust assay for monitoring GPCR activation with both full and partial agonists (FIG.

9C). Using cell lines stably expressing both receptor and sensor, an even better Z'-factor is expected and thus be sufficient to develop a high throuput screening (HTS) assay.

Since the fluorescent energy transfer of the invention is based on stimulatory principles such as BRET, a biosensor as described herein based on FRET instead of BRET would also be expected to function and is included within the scope of the present invention.

In summary, the above is believed to be the first real-time monitoring of agonist-promoted conformational changes of β-arr in living cells using a double-brilliance β-arr intramolecular BRET-based biosensor. The conformational rearrangement of the β-arr molecule and its interaction with other proteins reflects its transition from an inactive state to a biologically active state that follows its initial recruitment to activated GPCRs and involves the relative movement of the C- and N-terminus leading to a change in the BRET signal Beta-arrestin db sensors offer a robust assay for GPCR activation and characteristics (unimolecular structure, ratiometric signal and recruited to most GPCRs) that could be amenable to large-scale screening campaigns. In conclusion, double brilliance β-arr represents the first intramolecular BRET-based biosensor that allows the monitoring of protein conformational changes. This should lead the way to the development of similar tools to study other proteins believed to undergo significant conformational rearrangement linked to their function.

Although the present invention has been described by way of specific embodiments and examples thereof, with a particular focus on G protein-coupled receptors, it should be noted that it will be apparent to persons skilled in the art that modifications may be applied to the present particular embodiment without departing from the scope of the present invention.

LIST OF REFERENCES

1. Andrews D L, Demidov A A (1999) Resonance Energy Transfer. Chichester, UK: Wiley
2. Angers S, Salahpour A, Joly E, Hilairet S, Chelsky D, Dennis M, Bouvier M (2000) Detection of $β_2$-adrenergic receptor dimerization in living cells using bioluminescence resonance energy transfer (BRET). Proc Natl Acad Sci USA 97: 3684-3689
3. Azzi M, Charest P G, Angers S, Rousseau G, Kohout T, Bouvier M, Pineyro G (2003) β-Arrestin-mediated activation of MAPK by inverse agonists reveals distinct active conformations for G protein-coupled receptors. PNAS 100: 11406-11411
4. Bertrand L, Parent S, Caron M, Legault M, Joly E, Angers S, Bouvier M, Brown M, Houle B, Menard L (2002) The BRET2/arrestin assay in stable recombinant cells: a platform to screen for compounds that interact with G protein-coupled receptors (GPCRs). J Receptor Signal Transduction Res 22: 533-541
5. Charest P G, Bouvier M (2003) Palmitoylation of the V2 vasopressin receptor carboxyl tail enhances β-arrestin recruitment leading to efficient receptor endocytosis and ERK1/2 activation. J Biol Chem 278: 41541-41551
6. Chen W, Kirkbride K C, How T, Nelson C D, Mo J, Frederick J P, Wang X F, Lefkowitz R J, Blobe G C (2003) Beta-arrestin 2 mediates endocytosis to type III TFG-beta receptor and down-regulation of its signalling. Science 301 (5638): 1394-1397
7. Dalle S, Ricketts W, Imamura T, Vollenweider P, Olefsky J M (2001) Insulin and insulin-like growth factor I receptors utilize different G protein signalling components. J Biol Chem 276 (19): 15688-15695
8. Gurevich V V, Benovic J L (1993) Visual arrestin interaction with rhodopsin. Sequential multisite binding ensures strict selectivity toward lightactivated phosphorylated rhodopsin. Biol Chem 268: 11628-11638
9. Gurevich V V, Gurevich E V (2003) The new face of active receptor bound arrestin attracts new partners. Structure (Camb) 11: 1037-1042
10. Han M, Gurevich V V, Vishnivetskiy S A, Sigler P B, Schubert C (2001) Crystal structure of β-arrestin at 1.9 A°: possible mechanism of receptor binding and membrane translocation. Structure (Camb) 9: 869-880
11. Hebert T E, Moffett S, Morello J P, Loisel T P, Bichet D G, Barret C, Bouvier M (1996) A peptide derived from a $β_2$-adrenergic receptor transmembrane domain inhibits both receptor dimerization and activation. J Biol Chem 271: 16384-16392
12. Hirsch J A, Schubert C, Gurevich V V, Sigler P B (1999) The 2.8 A° crystal structure of visual arrestin: a model for arrestin's regulation. Cell 97: 257-269
13. Kovoor A, Celver J, Abdryashitov R I, Chavkin C, Gurevich V V (1999) Targeted construction of phosphorylation-independent β-arrestin mutants with constitutive activity in cells. J Biol Chem 274: 6831-6834
14. Leduc M, Breton B, Galés C, Le Gouill C, Bouvier M, Chemtob S, Heveker N (2009) Functional selectivity of natural and synthetic prostaglandin EP4 receptor ligands J Pharmacol Exp Ther. 331(1):297-307
15. Lefkowitz R J, Whalen E J (2004) β-arrestins: traffic cops of cell signalling. Curr Opin Cell Biol 16: 162-168
16. Lefkowitz R J, Shenoy S K (2005) Transduction of Receptor Signals by β-arrestins. Science 308: 512-517
17. Loening A M, Fenn T D, Wu A M, Gambhir S S. (2006) Consensus guided mutagenesis of Renilla luciferase yields enhanced stability and light output. Protein Eng Des Sel. 19(9):391-400.
18. Lin F T, Miller W E, Luttrell L M, Lefkowitz R J (1999) Feedback regulation of β-arrestin1 function by extracellular signal-regulated kinases. J Biol Chem 274: 15971-15974
19. Lin F T, Chen W, Shenoy S, Cong M, Exum S T, Lefkowitz R J (2002) Phosphorylation of β-arrestin2 regulates its function in internalization of b(2)-adrenergic receptors. Biochemistry 41: 10692-10699
20. Luttrell L M, Lefkowitz R J (2002) The role of β-arrestins in the termination and transduction of G-protein-coupled receptor signals. J Cell Sci 115: 455-465
21. Marrache A M et al (2002) Proinflammatory gene induction by plateletactivating factor mediated via its cognate nuclear receptor. J Immunol 169: 6474-6481
22. Mercier J F, Salahpour A, Angers S, Breit A, Bouvier M (2002) Quantitative assessment of b1- and $β_2$-adrenergic receptor homo- and heterodimerization by bioluminescence resonance energy transfer. J Biol Chem 277: 44925-44931
23. Milligan G (2004) Applications of bioluminescence- and fluorescence resonance energy transfer to drug discovery at G protein-coupled receptors. Eur J Pharm Sci 21: 397-405
24. Oakley R H, Laporte S A, Holt J A, Caron M G, Barak L S (2000) Differential affinities of visual arrestin, β-arrestin1, and β-arrestin2 for G proteincoupled receptors delineate two major classes of receptors. J Biol Chem 275: 17201-17210
25. Oakley R H, Laporte S A, Holt J A, Barak L S, Caron M G (2001) Molecular determinants underlying the forma- 25. tion of stable intracellular G proteincoupled receptor-3-arrestin complexes after receptor endocytosis. J Biol Chem 276: 19452-19460
26. Perroy J, Adam L, Qanbar R, Chemer S, Bouvier M (2003) Phosphorylationindependent desensitization of GABA(B) receptor by GRK4. EMBO J. 22: 3816-3824
27. Petaja-Repo U E, Hogue M, Bhalla S, Laperriere A, Morello J P, Bouvier M (2002) Ligands act as pharmacological chaperones and increase the efficiency of d-opioid receptor maturation. EMBO J. 21: 1628-1637
28. Pleskoff O, Treboute C, Brelot A, Heveker N, Seman M, Alizon M (1997) Identification of a chemokine receptor encoded by human cytomegalovirus as a cofactor for HIV-1 entry. Science 276: 1874-1878
29. Sambrook J, Fritsch E F, Maniatis T (1989) Molecular Cloning: A Laboratory Manual. New York: Cold Spring Harbor Laboratory Press
30. Terrillon S, Durroux T, Mouillac B, Breit A, Ayoub M A, Taulan M, Jockers R, Barberis C, Bouvier M (2003) Oxytocin and vasopressin V1a and V2 receptors form constitutive homo- and heterodimers during biosynthesis. Mol Endocrinol 17: 677-691
31. Vishnivetskiy S A, Hirsch J A, Velez M G, Gurevich Y V, Gurevich V V (2002) Transition of arrestin into the active receptor-binding state requires an extended interdomain hinge. J Biol Chem 277: 43961-43967
32. Xiao K, Shenoy S K, Nobles K, Lefkowitz R J (2004) Activation dependent conformational changes in β-arrestin 2. J Biol Chem 279: 55744-55753.
33. Zhang J, Campbell R E, Ting A Y, Tsien R Y (2002) Creating new fluorescent probes for cell biology. Nat Rev Mol Cell Biol 3: 906-918 Zhang J H, Chung T D, Oldenburg K R. (1999) A Simple Statistical Parameter for Use in Evaluation and Validation of High Throughput Screening Assays. J Biomol Screen. 4(2):67-73.

What is claimed is:

1. A resonance energy transfer (RET) biosensor comprising an arrestin tagged with a first and a second chromophore, wherein said first chromophore is a fluorophore and said second chromophore is a fluorophore or a bioluminophore.

2. The biosensor according to claim 1, wherein said arrestin is β-arrestin-1 (arrestin-2).

3. The biosensor according to claim 1, wherein said arrestin is β-arrestin-2 (arrestin-3).

4. The biosensor according to claim 1, wherein said arrestin is arrestin-1 or arrestin-4.

5. The biosensor according to claim 1, wherein said second chromophore is a bioluminophore and the RET is bioluminescence resonance energy transfer (BRET).

6. The biosensor according to claim 5, wherein said bioluminophore is *Renilla* luciferase or a mutant form of *Renilla* luciferase.

7. The biosensor according to claim 6, wherein said bioluminophore is RlucII (A55T/C124A/M185V).

8. The biosensor according to claim 5, which is selected from the group consisting of:
  Luc-β-arr-YFP,
  YFP-βarr-Luc,
  Luc-β-arr(3A)-YFP,
  Luc-β-arr(IV)-YFP,
  Luc-βarr(R169E)-YFP,
  mAmetrine-hβar1-RlucI,
  mAmetrine-hβarr2-RlucII,
  CFP-hβarr1-RlucII,
  CFP-hβarr2-RlucII,
  GFP10-hβarr1-RlucII, and
  GFP10-hβarr2-RlucII.

9. The biosensor according to claim 5, which is selected from the group consisting of:
  RLucII-GDLRRALENSHASGYQACGTGS (SEQ ID NO:5)-β-arrestin-1-CLEDPRVPVAT (SEQ ID NO:6)-YFP;
  RLucII-GDLRRALENSHASGYQACGTGS (SEQ ID NO:5)-β-arrestin-2-CLEDPRVPVAT (SEQ ID NO:6)-YFP;
  RLucII-GDLRRALENSHASGYQACGTGS (SEQ ID NO:5)-β-arrestin R169E-CLEDPRVPVAT (SEQ ID NO:6)-YFP;
  GFP10-GSAGT (SEQ ID NO:7)-β-arrestin-1-KLPAT (SEQ ID NO:8)-RlucII;
  GFP10-GSAGT (SEQ ID NO:7)-β-arrestin-2-KLPAT (SEQ ID NO:8)-RlucII;
  GFP10-GSAGT (SEQ ID NO:7)-β-arrestin-R169E-KLPAT (SEQ ID NO:8)-RlucII;
  CFP-GSAGT (SEQ ID NO:7)-β-arrestin-1-KLPAT (SEQ ID NO:8)-RlucII;
  CFP-GSAGT (SEQ ID NO:7)-β-arrestin-2-KLPAT (SEQ ID NO:8)-RlucII;
  CFP-GSAGT (SEQ ID NO:7)-β-arrestin-R169E-KLPAT (SEQ ID NO:8)-RlucII;
  mAmetrine-GSAGT (SEQ ID NO:7)-β-arrestin-1-KLPAT (SEQ ID NO:8)-RlucII;
  mAmetrine-GSAGT (SEQ ID NO:7)-β-arrestin-2-KLPAT (SEQ ID NO:8)-RlucII; and
  mAmetrine-GSAGT (SEQ ID NO:7)-β-arrestin R169E-KLPAT (SEQ ID NO:8)-RlucII.

10. The biosensor according to claim 1, wherein said first fluorophore is a fluorescent protein.

11. The biosensor according to claim 10, wherein said fluorescent protein is green fluorescent protein or a variant thereof.

12. The biosensor according to claim 10, wherein said fluorescent protein is yellow fluorescent protein (YFP), mAmetrine, cyan fluorescent protein (CFP), green fluorescent protein-2 (GFP-2), or green fluorescent protein-10 (GFP10).

13. The biosensor according to claim 1, wherein the first and second chromophores are independently attached to different positions on the arrestin, such positions being at the N-terminus, at the C-terminus, or at a position between the C- and N-termini of the arrestin.

14. The biosensor according to claim 1, wherein both said first and said second chromophores are fluorophores and the RET is fluorescence resonance energy transfer (FRET).

15. The biosensor according to claim 14, wherein the first chromophore is CFP or a variant thereof, and the second chromophore is a YFP or a variant thereof.

16. The biosensor according to claim 15, wherein the YFP is a non-circularly permuted sYFP2 or a circularly permuted sYFP2.

17. The biosensor according to claim 1, wherein the first chromophore, the second chromophore, or both the first and second chromophores are independently attached to the arrestin via a linker.

18. The biosensor according to claim 17, wherein the linker is a peptide linker.

19. The biosensor according to claim 18, wherein the peptide linker is 2 to 30 residues in length.

20. The biosensor according to claim 19, wherein the peptide linker is selected from the group consisting of GDLRRALENSHASAGYQACGTGS (SEQ ID NO:5), CLEDPRVPVAT (SEQ ID NO:6), GSAGT (SEQ ID NO:7), KLPAT (SEQ ID NO:8), GSAGTGSAGTGSAGT (SEQ ID NO:9), KLPATKLPATKLPAT (SEQ ID NO:10), and REAAAREAAAREAAAR (SEQ ID NO:11).

21. The biosensor according to claim 19, wherein the linker is attached to the arrestin at the C-terminus, at the N-terminus, to a position between the C and N-termini, or to a combination thereof.

* * * * *